(12) United States Patent
Bolotin

(10) Patent No.: US 7,790,140 B2
(45) Date of Patent: *Sep. 7, 2010

(54) COMPOSITIONS FOR DELIVERY OF THERAPEUTICS AND OTHER MATERIALS, AND METHODS OF MAKING AND USING THE SAME

(75) Inventor: Elijah M. Bolotin, Kirkland, WA (US)

(73) Assignee: PharmaIN Corporation, Seattle, WA (US)

( * ) Notice: Subject to any disclaimer, the term of this patent is extended or adjusted under 35 U.S.C. 154(b) by 1064 days.

This patent is subject to a terminal disclaimer.

(21) Appl. No.: 11/428,803

(22) Filed: Jul. 5, 2006

(65) Prior Publication Data

US 2006/0239924 A1 Oct. 26, 2006

Related U.S. Application Data

(63) Continuation of application No. 10/378,100, filed on Feb. 27, 2003, now Pat. No. 7,138,105.

(60) Provisional application No. 60/360,350, filed on Feb. 27, 2002.

(51) Int. Cl.
*A61K 51/00* (2006.01)
*A61M 36/14* (2006.01)

(52) U.S. Cl. .............. 424/1.65; 424/1.11; 424/1.49; 424/1.69; 424/1.73; 424/450; 424/489

(58) Field of Classification Search ............... 424/1.11, 424/1.37, 1.49, 1.61, 1.65, 1.69, 9.1, 9.3, 424/9.36, 9.4, 9.5, 9.6, 9.7, 9.8, 400, 450, 424/489, 1.73; 534/7, 10–16; 514/2, 6, 53, 514/54, 62; 206/223, 569, 570
See application file for complete search history.

(56) References Cited

U.S. PATENT DOCUMENTS

| | | | |
|---|---|---|---|
| 4,857,311 A | 8/1989 | Domb et al. | |
| 5,118,666 A | 6/1992 | Habener | |
| 5,120,712 A | 6/1992 | Habener | |
| 5,527,524 A | 6/1996 | Tomalia et al. | |
| 5,554,388 A | 9/1996 | Illum | |
| 5,593,658 A | 1/1997 | Bogdanov et al. | |
| 5,605,672 A | 2/1997 | Bogdanov et al. | |
| 5,614,492 A | 3/1997 | Habener | |
| 5,631,018 A | 5/1997 | Zalipsky et al. | |
| 5,661,025 A | 8/1997 | Szoka, Jr. et al. | |
| 5,663,387 A | 9/1997 | Singh | |
| 5,681,544 A | 10/1997 | Schmitt-Willich et al. | |
| 5,714,166 A | 2/1998 | Tomalia et al. | |
| 5,744,166 A | 4/1998 | Illum | |
| 5,763,585 A | 6/1998 | Nag | |
| 5,776,894 A | 7/1998 | Albert et al. | |
| 5,837,747 A | 11/1998 | Soon-Shiong et al. | |
| 5,871,710 A * | 2/1999 | Bogdanov et al. | .......... 424/1.65 |
| 5,891,418 A | 4/1999 | Sharma | |
| 5,929,031 A | 7/1999 | Kerwin et al. | |
| 5,958,909 A | 9/1999 | Habener | |
| 5,977,084 A | 11/1999 | Szoka, Jr. et al. | |
| 6,006,753 A | 12/1999 | Efendic | |
| 6,051,549 A | 4/2000 | Roberts et al. | |
| 6,113,946 A | 9/2000 | Szoka, Jr. et al. | |
| 6,124,273 A | 9/2000 | Drohan et al. | |
| 6,162,462 A | 12/2000 | Bolotin et al. | |
| 6,225,284 B1 | 5/2001 | Albert et al. | |
| 6,274,175 B1 | 8/2001 | Gombotz et al. | |
| 6,284,727 B1 | 9/2001 | Kim et al. | |
| 6,338,859 B1 | 1/2002 | Leroux et al. | |
| 6,348,069 B1 | 2/2002 | Vacanti et al. | |
| 6,365,173 B1 | 4/2002 | Domb et al. | |
| 6,395,299 B1 | 5/2002 | Babich et al. | |
| 6,443,898 B1 | 9/2002 | Unger et al. | |
| 6,447,753 B2 | 9/2002 | Edwards et al. | |
| 6,458,373 B1 | 10/2002 | Lambert et al. | |
| 6,468,532 B1 | 10/2002 | Hsei et al. | |
| 6,475,779 B2 | 11/2002 | Mathiowitz et al. | |
| 6,492,560 B2 | 12/2002 | Wilbur et al. | |
| 6,509,323 B1 | 1/2003 | Davis et al. | |
| 6,521,211 B1 | 2/2003 | Unger et al. | |
| 6,521,736 B2 | 2/2003 | Watterson et al. | |
| 6,579,851 B2 | 6/2003 | Goeke et al. | |
| 6,583,111 B1 | 6/2003 | DiMarchi et al. | |

(Continued)

FOREIGN PATENT DOCUMENTS

JP 10158195 6/1998

(Continued)

OTHER PUBLICATIONS

Caliceti et al., "Pharmacokinetic and biodistribution properties of poly(ethylene glycol)-protein conjugates," *Advanced Drug Delivery Reviews* 55: 1261-1277, 2003.

(Continued)

*Primary Examiner*—D L Jones
(74) *Attorney, Agent, or Firm*—Wilson Sonsini Goodrich & Rosati; Gerardo M. Castillo

(57) ABSTRACT

In part, the present invention is directed to biocompatible compositions comprising a carrier with a first metal binding domain, a metal ion, an active agent with second metal binding domain and optionally a protective chain covalently attached to the polymeric carrier.

24 Claims, 4 Drawing Sheets

U.S. PATENT DOCUMENTS

| | | |
|---|---|---|
| 6,586,524 B2 | 7/2003 | Sagara et al. |
| 6,589,549 B2 | 7/2003 | Shih et al. |
| 6,627,228 B1 | 9/2003 | Milstein et al. |
| 6,703,037 B1 | 3/2004 | Hubbell et al. |
| 6,703,359 B1 | 3/2004 | Young et al. |
| 6,706,689 B2 | 3/2004 | Coolidge et al. |
| 6,747,006 B2 | 6/2004 | Efendic |
| 6,828,303 B2 | 12/2004 | Kim et al. |
| 6,849,708 B1 | 2/2005 | Habener |
| 6,884,628 B2 | 4/2005 | Hubbell et al. |
| 6,894,024 B2 | 5/2005 | Coolidge et al. |
| 6,899,883 B2 | 5/2005 | Dupre |
| 6,982,248 B2 | 1/2006 | Coolidge, et al. |
| 6,998,137 B2 | 2/2006 | Shih et al. |
| 7,049,284 B2 | 5/2006 | Drucker |
| 7,101,843 B2 | 9/2006 | Glaesner et al. |
| 7,138,105 B2 * | 11/2006 | Bolotin .................... 424/9.36 |
| 7,138,486 B2 | 11/2006 | Habener et al. |
| 7,144,863 B2 | 12/2006 | DeFelippis et al. |
| 7,199,217 B2 | 4/2007 | DiMarchi et al. |
| 7,259,233 B2 | 8/2007 | Dodd et al. |
| 7,285,529 B2 | 10/2007 | Summerton |
| 7,329,644 B2 | 2/2008 | Saviano et al. |
| 7,534,449 B2 | 5/2009 | Saltzman et al. |
| 2002/0015737 A1 | 2/2002 | Shih et al. |
| 2002/0132254 A1 | 9/2002 | Twu |
| 2003/0050237 A1 | 3/2003 | Kim et al. |
| 2003/0119734 A1 | 6/2003 | Flink et al. |
| 2003/0220251 A1 | 11/2003 | Knudsen et al. |
| 2003/0224974 A1 | 12/2003 | Bolotin |
| 2003/0229034 A1 | 12/2003 | Waugh et al. |
| 2004/0092432 A1 | 5/2004 | During et al. |
| 2004/0162241 A1 | 8/2004 | Efendic |
| 2004/0197369 A1 | 10/2004 | Hubbell et al. |
| 2004/0209803 A1 | 10/2004 | Baron et al. |
| 2004/0220105 A1 | 11/2004 | Jensen et al. |
| 2004/0235726 A1 | 11/2004 | Jakubowski et al. |
| 2004/0266683 A1 | 12/2004 | Hathaway et al. |
| 2005/0008661 A1 | 1/2005 | Fereira et al. |
| 2005/0014681 A1 | 1/2005 | Minamitake et al. |
| 2005/0143303 A1 | 6/2005 | Quay et al. |
| 2005/0148497 A1 | 7/2005 | Khan et al. |
| 2005/0159356 A1 | 7/2005 | Dong et al. |
| 2005/0215475 A1 | 9/2005 | Ong et al. |
| 2005/0239705 A1 | 10/2005 | Dake et al. |
| 2005/0260259 A1 | 11/2005 | Bolotin |
| 2006/0003935 A1 | 1/2006 | Pan et al. |
| 2006/0019874 A1 | 1/2006 | Radhakrishnan et al. |
| 2006/0030838 A1 | 2/2006 | Gonnelli |
| 2006/0057137 A1 | 3/2006 | Steiness |
| 2006/0074025 A1 | 4/2006 | Quay et al. |
| 2006/0093660 A1 | 5/2006 | Bolotin |
| 2006/0128627 A1 | 6/2006 | Goke et al. |
| 2006/0172091 A1 | 8/2006 | Ong et al. |
| 2006/0178304 A1 | 8/2006 | Juul-Mortensen et al. |
| 2006/0183682 A1 | 8/2006 | Juul-Mortensen |
| 2006/0199763 A1 | 9/2006 | Knudsen et al. |
| 2006/0247167 A1 | 11/2006 | Schlein et al. |
| 2006/0286129 A1 | 12/2006 | Sarubbi |
| 2007/0041951 A1 | 2/2007 | Egan et al. |
| 2007/0141006 A1 | 6/2007 | Livoreil et al. |
| 2007/0141145 A1 | 6/2007 | Castillo et al. |
| 2007/0244296 A1 | 10/2007 | Tomalia et al. |
| 2007/0298006 A1 | 12/2007 | Tomalia et al. |
| 2008/0015263 A1 | 1/2008 | Bolotin et al. |
| 2009/0053169 A1 | 2/2009 | Castillo et al. |

FOREIGN PATENT DOCUMENTS

| | | |
|---|---|---|
| WO | WO-94/05203 | 3/1994 |
| WO | WO-97/33552 | 9/1997 |
| WO | WO-98/42383 | 10/1998 |
| WO | WO 01/28569 A1 | 4/2001 |
| WO | WO-01/39815 | 6/2001 |
| WO | WO 01/87925 A2 | 11/2001 |
| WO | WO 01/39815 A3 | 1/2002 |
| WO | WO 01/87925 A3 | 8/2002 |
| WO | WO 03/072143 A1 | 9/2003 |
| WO | WO 2004/022004 A2 | 3/2004 |
| WO | WO 2004/022004 A3 | 12/2004 |
| WO | WO 2005/084180 A2 | 9/2005 |
| WO | WO 2005/084180 A3 | 12/2005 |
| WO | WO 2007/024899 A2 | 3/2007 |
| WO | WO 2007/030706 A1 | 3/2007 |
| WO | WO 2007/048190 A1 | 5/2007 |
| WO | WO 2007/056681 A2 | 5/2007 |
| WO | WO 2007/082331 A1 | 7/2007 |
| WO | WO 2007/024899 A3 | 11/2007 |
| WO | WO 2007/056681 A3 | 4/2008 |

OTHER PUBLICATIONS

Terpe, "Overview of tag protein fusions: from molecular and biochemical fundamentals to commercial systems," *Appl. Microbiol. Biotechnol.* 60: 523-533, 2003.

Van Broekhoven et al.: "A novel system for convenient detection of low-affinity receptor-ligand interactions: Chelator-lipid liposomes engrafted with recombinant CD4 bind to cells expressing MHC class II," *Immunology and Cell Biology*, pp. 274-284, 2001.

Prosser et al.: "Novel Chelate-Induced Magnetic Alignment of Biological Membranes," Biophysical Journal, vol. 75, pp. 2163-2169, Nov. 1998.

Otto and Birkenmeier, "Recognition and Separation of Isoenzymes by Metal Chelates: Immobilized Metal Ion Affinity Partitioning of Lactate Dehydrogenase Isoenzymes", *Journal of Chromatography*, 644: 25-33 (1993).

Suginoshita et al., "Liver Targeting of Interferon-β with a Liver-Affinity Polysaccharide Based on Metal Coordination in Mice", *Journal of Pharmacology and Experimental Therapeutics*, 298(2): 805-811 (2001).

Supplementary Partial European Search Report for Corresponding European Application No. EP 03716207, dated Nov. 22, 2005.

International Search Report for Corresponding PCT Application No. PCT/US05/14128, dated May 26, 2006.

International Search Report for PCT/US03/05937 Completed on Jun. 16, 2003 and mailed on Jul. 24, 2003.

Barton, J. Protective Groups in Organic Chemistry. McOmie, ed. New York, NY: Plenum Press, 1973, chapter 2.

Greene, et al. Protective Groups in Organic Synthesis, 2nd Edition. New York, NY: Wiley & Sons, 1991, chapter 7.

Hrkach, et al. Poly(L-lactic acid-co-amino acid) graft copolymers: A class of functional biodegradable biomaterials. Hydrogel and Biodegradable Polymers for Bioapplications, ACS Symposium Series No. 627. Ottenbrite, et al., eds. American Chemical Society, 1996: 93-101 (chapter 8).

Hrkach, et al. Synthesis of poly(L-lactic acid-co-L-lysine) graft copolymers. Macromolecules. 1995; 28: 4736-9.

Leonard, et al. Trimethylene Bridges as Synthetic Spacers for the Detection of Intramolecular Interaction. Accounts of Chem. Res. 1979; 12:423.

March. Quantitative Treatments of the Effect of Structure on Reactivity. Advanced Organic Chemistry. New York, NY: McGraw Hill Book Company, 1977, 251-9.

Weast, R. Periodic table of elements, CAS version. Handbook of Chemistry and Physics, 67th Edition. Boca Raton, FL: CRC Press, 1986-87.

Cunninghanm, et al. Dimerization of human growth hormone by zinc. Science. Aug. 2, 1991; 253(5019):545-8.

Tabata, et al. Growth factor release from amylopectin hydrogel based on copper coordination. J Control Release. Dec. 4, 1998;56(1-3):135-48.

Tabata, et al. Targeting of tumor necrosis factor to tumor by use of dextran and metal coordination. J Control Release. May 20, 1999;59(2):187-96.

Ahrén, et al. Improved glucose tolerance and insulin secretion by inhibition of dipeptidyl peptidase IV in mice. Eur. J. Pharmacol. 2000; 404(1-2):239-45.

Bogdanov, et al. A new macromolecule as a contrast agent for MR angiography: preparation, properties, and animal studies. Radiology. 1993; 187(3):701-6.

Bogdanov, et al. Long-circulating blood pool imaging agents. Adv Drug Del Revs. 1995; 16:335-348.

Bonner-Weir, et al. Imaging the Pancreatic Beta Cell. 1999; http://www.niddk.nih.gov/fund/reports/beta_imaging_report_2.htm.

Brand, et al. Pharmacological treatment of chronic diabetes by stimulating pancreatic beta-cell regeneration with systemic co-administration of EGF and gastrin. Pharmacol Toxicol. 2002; 91(6):414-20.

Bulotta, et al. Cultured pancreatic ductal cells undergo cell cycle re-distribution and beta-cell-like differentiation in response to glucagon-like peptide-1. J. Mol. Endocrinol. 2002; 29(3):347-60.

Buteau, et al. Glucagon-like peptide-1 promotes DNA synthesis, activates phosphatidylinositol 3-kinase and increases transcription factor pancreatic and duodenal homeobox gene 1 (PDX-1) DNA binding activity in beta (INS-1)-cells. Diabetologia. 1999; 42(7):856-64.

Callahan, et al. Preclinical evaluation and phase I clinical trial of a 99mTc-labeled synthetic polymer used in blood pool imaging. AJR Am J Roentgenol. 1998; 171(1):137-43.

Clark, D. Guide for Care of Use of Laboratory Animals. National Research Council. 1996.

Druncker, D. Enhancing incretin action for the treatment of type 2 diabetes. Diabetes Care. 2003; 26(10):2929-40.

Ettaro, et al. Cost-of-illness studies in diabetes mellitus. Pharmacoeconomics. 2004; 22(3):149-64.

Farilla, et al. Glucagon-like peptide 1 inhibits cell apoptosis and improves glucose responsiveness of freshly isolated human islets. Endocrinology. 2003; 144(12):5149-58.

Gappa, et al. The effect of zinc-crystallized glucagon-like peptide-1 on insulin secretion of macroencapsulated pancreatic islets. Tissue Eng. 2001; 7(1):35-44.

Gupta, et al. Inflammation: imaging with methoxy poly(ethylene glycol)-poly-L-lysine-DTPA, a long-circulating graft copolymer. Radiology. 1995; 197(3):665-9.

Hui, et al. Glucagon-like peptide 1 induces differentiation of islet duodenal homeobox-1-positive pancreatic ductal cells into insulin-secreting cells. Diabetes. 2001; 50(4):785-96.

Lapidot, et al. Use of esters of N-hydroxysuccinimide in the synthesis of N-acylamino acids. J Lipid Res. 1967; 8(2): 142-5.

List of the abbreviation utilized by Organic Chemists of Ordinary Scill in the art. Journal of Organic Chemistry. First issue of each volume. (2005).

MicroGD™. Accessed at http://pharmain.com/MacroGdPage.html. Accessed Feb. 29, 2008.

Nielsen, et al. Pharmacology of exenatide (synthetic exendin-4) for the treatment of type 2 diabetes. Curr. Opinion Investig. Drugs. 2003; 4(4):401-5.

Perry, et al. The glucagon-like peptides: a double-edged therapeutic sword? Trends in Pharmacol. Sci. 2003; 24(7):377-83.

Röstin, et al. B-Domain deleted recombinant coagulation factor VIII modified with monomethoxy polyethylene glycol. Bioconjug Chem. 2000; 11(3): 387-396.

Scrocchi, et al. Identification of glucagon-like peptide 1 (GLP-1) actions essential for glucose homeostasis in mice with disruption of GLP-1 receptor signaling. Diabetes. 1998; 47(4):632-9.

Shapiro, et al. Clinical islet transplant: current and future directions towards tolerance. Immunol. Rev. 2003; 196:219-36.

Tourrel, et al. Glucagon-like peptide-1 and exendin-4 stimulate beta-cell neogenesis in streptozotocin-treated newborn rats resulting in persistently improved glucose homeostasis at adult age. Diabetes. 2001; 50(7):1562.

Urusova, et al. GLP-1 inhibition of pancreatic islet cell apoptosis. Trends Endocrinol Metab. 2004; 15(1):27-33.

Wiedeman, et al. Dipeptidyl peptidase IV inhibitors for the treatment of impaired glucose tolerance and type 2 diabetes. Curr. Opinion Investig. Drugs. 2003; 4(4):412-420.

Xu, et al. Exendin-4 stimulates both beta-cell replication and neogenesis, resulting in increased beta-cell mass and improved glucose tolerance in diabetic rats. Diabetes. 1999; 48(12):2270-6.

Bolotin, E. U.S. Appl. No. 60/464,601, entitled "Compositions for Treatment With Factor Viii, and Methods of Making and Using the Same," filed on Apr. 22, 2003.

Bolotin, E. U.S. Appl. No. 60/360,350, entitled "Compositions for delivery of peptides and proteins," filed on Feb. 27, 2002.

Quay et al. U.S. Appl. No. 60/532,337, entitled "Intranasal administration of glucose-regulating peptides" filed on Dec. 26, 2003.

European search report dated Nov. 29, 2005 for Application No. 03716207.

International search report dated Jul. 24, 2003 for PCT Application No. US03/05937.

International search report dated May 26, 2006 for PCT Application No. US05/14128.

International search report dated Jul. 7, 2008 for PCT Application No. US07/88010.

Porath, et al. Metal chelate affinity chromatography, a new approach to protein fractionation. Nature. Dec. 18, 1975;258(5536):598-9.

* cited by examiner

COMPOSITIONS FOR DELIVERY OF THERAPEUTICS AND OTHER MATERIALS, AND METHODS OF MAKING AND USING THE SAME

RELATED APPLICATION INFORMATION

This application is a continuation of U.S. patent application Ser. No. 10/378,100 filed Feb. 27, 2003, which claims the benefit of priority under 35 U.S.C. 119(e) to U.S. Provisional Application No. 60/360,350 filed Feb. 27, 2002.

INTRODUCTION

The development of new drugs, formulations and other systems for administration of physiologically active peptides and proteins and other therapeutics and materials is driven by the need to provide these peptides or proteins or other materials to achieve the desirable physiological effects. With respect to peptides and proteins, many of them have been observed to be unstable in the gastro-intestinal tract and therefore may need to be stabilized or protected or delivered via systemic circulation. In addition, peptides and proteins that have low molecular masses tend to have short biological half-lives due to their efficient removal from systemic circulation via kidneys. For example, a fraction of these peptides and proteins can also be removed via reticulo-endothelial uptake due to recognition by monocyte/macrophages or as a result of opsonization by complement components. Many peptides and proteins can also lose their activity in vivo due to proteolysis (peptide bond cleavage).

In part to circumvent these undesirable effects, a drug delivery system may be used. There are several drug delivery strategies that can be useful for peptide and protein delivery in vivo. First, a continuous systemic infusion of drug via a pump can be employed. This strategy is proven efficient in clinical practice but may be impractical for outpatients requiring high levels of mobility, associated disadvantages of quality of life and potential intravenous (I.V.) line infections.

Second, peptides and proteins can be included in an implantable pump comprised of a capsule with a membrane allowing diffusion of the drug, for example, at a desirable release rate. Due to limited volume of these capsules, peptides and proteins are often used in a concentrated formulation, which leads to a loss of solubility due to aggregation and potential loss of specific activity. In most cases, the drug is usually released into the extracellular space and distributed in lymphatics. Overall concentration of peptide or protein may be affected by local lymph node activity and the efficacy of lymph node drainage of the implantation site. There is also a potential of host reaction to capsule material but in general, this side effect is infrequent.

Third, the drug release system can be made biodegradable as a result of encapsulation or inclusion into degradable drug delivery vehicles or carriers, e.g. polymeric matrices, particles or membrane vesicles (liposomes). These delivery systems are usually either implantable or injectable. Implantable drug delivery systems are often placed under the epidermis where the components of the system are usually slowly degraded as a result of biological activity of surrounding cells (i.e. as a result of the release of enzymes degrading chemical bonds that hold these implants together).

In part, the present invention is directed towards novel drug delivery systems, and methods of making and using the same.

SUMMARY OF INVENTION

In part, the present invention is directed to the use of metal bridges to connect a carrier and an active agent of interest. In certain instances, the subject compositions provide a means of achieving sustained release of an active agent after administration to a patient. As used herein, a "metal bridge" comprises the metal binding domain (MBD) of the carrier, the MBD of the active agent, and the metal that is chelated to both of them. It may be the case that the metal bridge may comprise more than a single metal ion (i.e., multiple metal ions) with bridging ligands, provided that the MBDs of the carrier and active agent are capable of being connected through the metal ions and bridging ligand.

In part, the present invention is directed to a drug delivery system involving a polymeric carrier to which a drug may associate via a metal ion. It has been observed that polymeric carriers bearing chelated metal ion can bind biologically active peptides and proteins in the absence or presence of plasma proteins. The subject compositions, and methods of making and using the same, may achieve a number of desirable results and features, one or more of which (if any) may be present in any particular embodiment of the present invention: 1) protecting peptides and proteins and other associated drugs from the interaction with other macromolecules and cells; 2) decreasing undesirable immunogenicity of the carrier or peptide/protein/drug; 3) prolonging biological half-life of peptides and proteins and drugs in vivo (e.g. for decreasing glomerular filtration in kidneys, decreasing kidney and liver uptake, decreasing macrophage uptake etc); 4) stabilizing peptides/proteins/drugs by complexation with metal ion and carrier. One potential advantage of the metal binding domain of the present invention is to afford labile binding with peptides and proteins and other drugs which are capable of forming coordination bonds with metal ions (e.g., Zn and Ni). In many instances, coordinate bonding affords reversible dissociation of the peptide or protein or drug from the polymeric carrier. It may be possible to affect the dissociation rate by modulating with competitive ligands for the metal ion, such as imidazole or nitrilotriacetic acid (NTA).

In certain embodiments, the present invention relates to a biocompatible composition comprising: (i) a carrier with a metal binding domain (MBD); (ii) a metal ion chelated to the MBD; and (iii) an active agent with a MBD chelated to the metal ion, wherein after administration of the composition to a patient, the active agent is released in a sustained manner. It is understood that not all of the active agents in a sample of the composition will necessarily be attached to the carrier through the metal ion, but that some portion of the active agent may be combined with the carrier. Likewise, it is understood that not all of the metal binding domains attached to the carrier will chelate a metal ion, and that not all of the metal ions bound to a metal binding domain will form a coordinate bond with an active agent.

In a further embodiment, the present invention relates to the composition described above wherein the carrier is one of the following: polymer, micelle, reverse micelle, liposome, emulsion, hydrogel, microparticle, nanoparticle, microsphere, or solid surface. In a further embodiment, the carrier is a biocompatible polymer. In a further embodiment, the carrier is a polymer having a molecular weight ranging from about 100 to about 1,000,000 daltons. In a further embodiment, the carrier is a polymer having a molecular weight ranging from about 10,000 to about 250,000 daltons. In a further embodiment, the carrier comprises a poly amino acid. In a further embodiment, the carrier comprises poly-lysine.

In a further embodiment, the present invention relates to the above described composition wherein the carrier comprises protective side chains. In a further embodiment, the protective side chain comprises poly(ethylene glycol). In a further embodiment, the protective side chain comprises alkoxy poly(ethylene glycol). In a further embodiment, the protective side chain comprises methoxy poly(ethylene glycol) (MPEG).

In a further embodiment, the present invention relates to the above described composition wherein the metal binding domain comprises a nitrogen containing poly carboxylic acid. In a further embodiment, the metal binding domain comprises one or more of the following moieties: N-(hydroxy-ethyl)ethylenediaminetriacetic acid; nitrilotriacetic acid (NTA); ethylene-bis(oxyethylene-nitrilo)tetraacetic acid; 1,4,7,10-tetraazacyclodo-decane-N,N',N'',N'''-tetraacetic acid; 1,4,7,10-tetraaza-cyclododecane-N,N',N''-triacetic acid; 1,4,7-tris(carboxymethyl)-10-(2'-hydroxypropyl)-1,4,7,10-tetraazocyclodecane; 1,4,7-triazacyclonane-N,N',N''-triacetic acid; 1,4,8,11-tetraazacyclotetra-decane-N,N',N'',N'''-tetraacetic acid; diethylenetriamine-pentaacetic acid (DTPA); ethylenedicysteine; bis(aminoethanethiol)carboxylic acid; triethylenetetraamine-hexaacetic acid; ethylenediamine-tetraacetic acid (EDTA); 1,2-diaminocyclohexane-N,N,N',N'-tetraacetic acid; or polypeptide. In a further embodiment, the polypeptide in the metal binding domain has the formula: $(AxHy)_p$ where A is any amino acid residue, H is histidine, x is an integer from 0-6; y is an integer from 1-6; and p is an integer from 1-6.

In a further embodiment, the present invention relates to the above described composition wherein the metal ion is a transition metal ion. In a further embodiment, the metal ion is one or more of the following: $Zn^{2+}$, $Ni^{2+}$, $Co^{2+}$, $Fe^{2+}$, $Mn^{2+}$, or $Cu^{2+}$.

In a further embodiment, the present invention relates to the above described composition wherein the active agent is one of the following: a diagnostic, targeting moiety, or therapeutic agent. In a further embodiment, the present invention relates to the above described composition wherein more than one type of active agent forms a coordinate bond with the metal binding domain of the polymeric carrier. In a further embodiment, the active agent is a therapeutic agent comprising a protein, peptide, peptidomimetic, deoxyribonucleic acid, ribonucleic acid, oligonucleotide, other nucleic acid, oligosaccharide, antibody or proteoglycan.

In a further embodiment, the present invention relates to the above described composition wherein the carrier comprises poly-L-lysine, the protective side chain comprises MPEG, the metal binding domain comprises NTA, the metal ion is $Ni^{2+}$, and the active agent is rhGH.

In a further embodiment, the present invention relates to the above described composition wherein the carrier comprises poly-L-lysine, the protective side chain comprises MPEG, the metal binding domain comprises NTA, the metal ion is $Zn^{2+}$, and the active agent is rhGH.

In another embodiment, the present invention relates to a pharmaceutical composition comprising any of the above described compositions. In a further embodiment, the pharmaceutical composition is an aerosol.

In another embodiment, the present invention relates to a composition comprising: a carrier with a metal binding domain (MBD), a metal ion chelated to the MBD of the carrier, one or more protective side chains covalently bonded to the carrier, and an active agent with a MBD chelated to the metal ion. In a further embodiment, the carrier comprises a polymer. In a further embodiment, the protective sidechain comprises poly(ethylene glycol). In a further embodiment, the protective sidechain comprises alkoxy poly(ethyleneglycol). In a further embodiment, the protective sidechain comprises methoxy poly(ethyleneglycol) (MPEG). In a further embodiment, the active agent is a therapeutic agent. In a further embodiment, the active agent is a peptide or protein.

The present invention provides a number of methods of making the subject compositions. Examples of such methods include those described in the Exemplification below.

In another embodiment, the present invention relates to a method of treatment, comprising administering any of the above described compositions.

In another embodiment, the present invention relates to a kit comprising a composition comprising: (i) a carrier with a MBD; (ii) a metal ion chelated to the MBD of the carrier; and (iii) an active agent with a MBD chelated to the metal ion. Uses for such kits include, for example, therapeutic applications. Such kits may have a variety of uses, including, for example, imaging, targeting, diagnosis, therapy, vaccination, and other applications.

In another aspect, the compositions of the present invention may be used in the manufacture of a medicament for any number of uses, including for example treating any disease or other treatable condition of a patient. In still other aspects, the present invention is directed to a method for formulating biocompatible compositions of the present invention in a pharmaceutically acceptable carrier.

These embodiments of the present invention, other embodiments, and their features and characteristics, will be apparent from the description, drawings and claims that follow.

DETAILED DESCRIPTION OF INVENTION

Definitions

Figure 1:
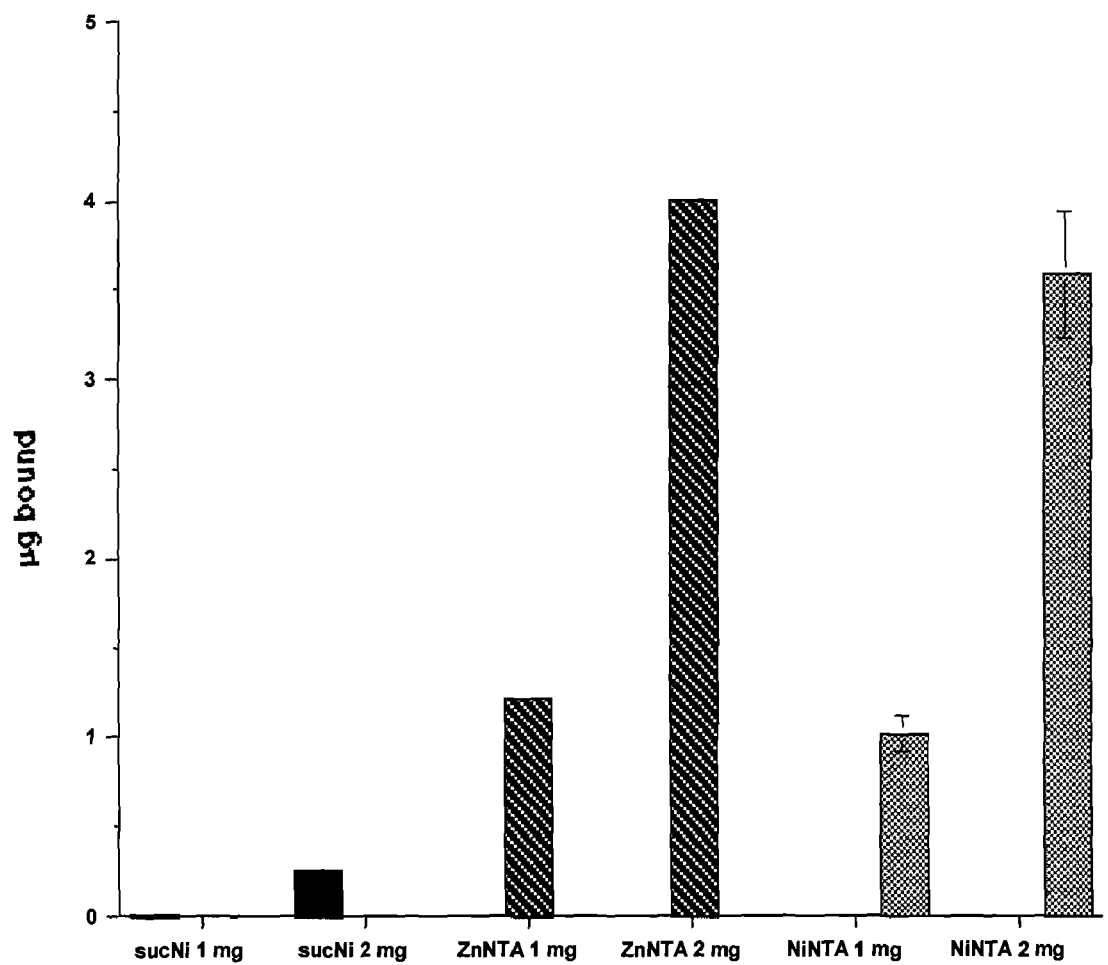
FIG. 1 depicts a graph showing the binding of hrGH to polymers in the presence of Zn and Ni cations. Size-separation on Centricon YM-100 membrane suggests that approximately 1 mg of rhGH binds to 100 mg of MPEGs-PL-ZnNTA.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used to refer to one or to more than one (i.e., to at least one) of the grammatical object of the article. By way of example, "an element" means one element or more than one element.

The term "plurality" means more than one.

The terms "comprise" and "comprising" are used in the inclusive, open sense, meaning that additional elements may be included.

The term "including" is used to mean "including but not limited to". "Including" and "including but not limited to" are used interchangeably.

The term "backbone polymer" is art-recognized and refers to any linear or branched polymer or copolymer from which pendant side chains may be chemically linked.

The term "carrier" refers to any substance capable of supporting a metal binding domain which in turn chelate at least one metal ion which in turn coordinates at least one active agent.

The term "protective side chain" is art recognized and refers to any side chain chemical moiety chemically linked to the backbone polymer or other type of carrier that is capable of providing protection for a therapeutic agent also associated with the backbone polymer or other type of carrier. In some instances, the protective side chain is capable of protecting the therapeutic agent through sterics. In certain embodiments, the protective side chain is linear or branched polymer or copolymer.

The term "chemically linked" is art-recognized and refers to two atoms or chemical moieties bonded together through either a covalent, ionic, or hydrogen bond.

The term "metal binding domain" is art-recognized and refers to any conformational arrangement of several chemical groups that is capable of forming a complex between the metal ion and the chemical groups by coordinate bonds.

The term "chelated" is art-recognized and refers to a metal ion coordinated with a Lewis Base of a chemical moiety. In certain instances, when the moiety would be deemed a bidentate ligand, the metal ion and the moiety form a ring.

The term "chelating group" is art-recognized and refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" are art-recognized and refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

The term "non-liposomic carrier" refers to carriers that do not have the properties of liposomes. It is understood by those ordinarily skilled in the art that liposomes are vesicles with an internal cavity and an external surface, and further that the location of a MBD in either the internal or external portion would effect the properties of the compositions of the present invention. For example, in certain applications an external MBD would be desirable for the slow release of a therapeutic agent.

The term "biocompatible composition" as used herein means that the composition in question, upon implantation in a subject, does not elicit a detrimental response sufficient to result in the rejection of the composition or to render it inoperable, for example through degradation. To determine whether any subject composition is biocompatible, it may be necessary to conduct a toxicity analysis. Such assays are well known in the art. One non-limiting example of such an assay for analyzing a composition of the present invention would be performed with live carcinoma cells, such as GT3TKB tumor cells, in the following manner: various amounts of subject compositions are placed in 96-well tissue culture plates and seeded with human gastric carcinoma cells (GT3TKB) at 104/well density. The degraded products are incubated with the GT3TKB cells for 48 hours. The results of the assay may be plotted as % relative growth versus amount of compositions in the tissue-culture well. In addition, compositions of the present invention may also be evaluated by well-known in vivo tests, such as subcutaneous implantations in rats to confirm that they do not cause significant levels of irritation or inflammation at the subcutaneous implantation sites.

The term "treating" is art recognized and includes preventing a disease, disorder or condition from occurring in a patient which may be predisposed to the disease, disorder and/or condition but has not yet been diagnosed as having it; inhibiting the disease, disorder or condition, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected. Treating includes, without limitation, use of the subject compositions with a diagnostic for diagnostic purposes as well as a targeting moiety or an antigen.

The term "active agent" includes without limitation, therapeutic agents, diagnostics, targeting moieties, and anitgens.

The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

A "diagnostic" or "diagnostic agent" is any chemical moiety that may be used for diagnosis. For example, diagnostic agents include imaging agents containing radioisotopes such as indium or technetium; contrasting agents containing iodine or gadolinium; enzymes such as horse radish peroxidase, GFP, alkaline phosphatase, or β-galactosidase; fluorescent substances such as europium derivatives; luminescent substances such as N-methylacrydium derivatives or the like.

"Diagnosis" is intended to encompass diagnostic, prognostic, and screening methods.

The term "targeting moiety" refers to any molecular structure which assists the construct in localizing to a particular target area, entering a target cell(s), and/or binding to a target receptor. For example, lipids (including cationic, neutral, and steroidal lipids, virosomes, and liposomes), antibodies, lectins, ligands, sugars, steroids, hormones, nutrients, and proteins may serve as targeting moieties.

A "target" shall mean a site to which targeted constructs bind. A target may be either in vivo or in vitro. In certain embodiments, a target may be a tumor (e.g., tumors of the brain, lung (small cell and non-small cell), ovary, prostate, breast and colon as well as other carcinomas and sarcomas). In other embodiments, a target may be a site of infection (e.g., by bacteria, viruses (e.g., HIV, herpes, hepatitis) and pathogenic fungi (*Candida sp.* ). In still other embodiments, a target may refer to a molecular structure to which a targeting moiety binds, such as a hapten, epitope, receptor, dsDNA fragment, carbohydrate or enzyme. Additionally, a target may be a type of tissue, e.g., neuronal tissue, intestinal tissue, pancreatic tissue etc.

The term "antigen" refers to any molecule or compound that specifically binds to an antigen binding site.

The term "antigen binding site" refers to a region of an antibody construct that specifically binds an epitope on an antigen.

The term "antibody" is art-recognized and intended to include whole antibodies, e.g., of any isotype (IgG, IgA, IgM, IgE, etc.), and includes fragments thereof which are also specifically reactive with a vertebrate, e.g., mammalian, protein. Antibodies may be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention may include polyclonal, monoclonal or other purified preparations of antibodies and recombinant antibodies.

The phrases "systemic administration," "administered systemically," "peripheral administration" and "administered peripherally" are art-recognized, and include the administration of a subject composition or other material at a site remote from the disease being treated. Administration of a subject composition directly into, onto or in the vicinity of a lesion of the disease being treated, even if the composition is subsequently distributed systemically, may be termed "local" or "topical" or "regional" administration, other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of the therapeutic agent that, when bridged through a metal ion to a carrier of the present invention, produces some desired effect at a reasonable benefit/risk ratio applicable to any medical treatment. In certain embodiments, the term refers to that amount necessary or sufficient to eliminate, reduce or maintain (e.g., prevent the spread of) a tumor or other target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, the term refers to that amount necessary or sufficient for a use of the subject compositions described herein.

The term "naturally-occurring", as applied to an object, refers to the fact that an object may be found in nature. For example, a carrier that may be isolated from a source in nature and which has not been intentionally modified by man in the laboratory is naturally-occurring.

The term "porous particles" refers to particles having a total mass density less than about $0.4$ $g/cm^3$. The mean diameter of the particles can range, for example, from about 100 nm to 15 µm, or larger depending on factors such as particle composition.

The term "ligand" is art-recognized and refers to a species that interacts in some fashion with another species. In one example, a ligand may be a Lewis base that is capable of forming a coordinate bond with a Lewis Acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The terms "labile" and "non-labile" are art-recognized and are usually used in this context in reference to a ligand bonded to a metal ion. Without intending to limit or modify the definition for the term as it is known in the art, a labile ligand may be understood to be a ligand whose bond to the metal ion is expected to break under certain circumstances.

The term "cis" is art-recognized and refers to the arrangement of two atoms or groups around a central metal atom such that the atoms or groups are next to each other.

The term "trans" is art-recognized and refers to the arrangement of two atoms or groups around a central metal atom such that the atoms or groups are not next to each other and are on opposite sides of the central metal atom.

The terms "Lewis acid" and "Lewis acidic" are art-recognized and refer to chemical moieties which can accept a pair of electrons from a Lewis base as defined above.

The terms "Lewis base" and "Lewis basic" are art-recognized and generally refer to a chemical moiety capable of donating a pair of electrons under certain reaction conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. In certain examples, a Lewis base may consist of a single atom, such as oxide ($O^{2-}$). In certain, less common circumstances, a Lewis base or ligand may be positively charged. A Lewis base, when coordinated to a metal ion, is often referred to as a ligand. Further description of ligands relevant to the present invention is presented herein.

The term "covalent bond" is art-recognized and refers to a bond between two atoms where electrons are attracted electrostatically to both nuclei of the two atoms, and the net effect of increased electron density between the nuclei counterbalances the internuclear repulsion. The term covalent bond includes coordinate bonds when the bond is with a metal ion.

The term "coordination" is art-recognized and refers to an interaction in which one multi-electron pair donor coordinatively bonds (is "coordinated") to one metal ion.

The term "coordinate bond" is art-recognized and refers to an interaction between an electron pair donor and a coordination site on a metal ion leading to an attractive force between the electron pair donor and the metal ion. The use of this term is not intended to be limiting, in so much as certain coordinate bonds may also be classified as having more or less covalent character (if not entirely covalent character) depending on the nature of the metal ion and the electron pair donor.

The term "coordination site" is art-recognized and refers to a point on a metal ion that can accept an electron pair donated, for example, by a liquid or chelating agent.

The term "free coordination site" is art-recognized and refers to a coordination site on a metal ion that is vacant or occupied by a species that is weakly donating. Such species is readily displaced by another species, such as a Lewis base.

The term "coordination number" is art-recognized and refers to the number of coordination sites on a metal ion that are available for accepting an electron pair.

The term "coordination geometry" is art-recognized and refers to the manner in which coordination sites and free coordination sites are spatially arranged around a metal ion. Some examples of coordination geometry include octahedral, square planar, trigonal, trigonal biplanar and others known to those of skill in the art.

The term "complex" is art-recognized and refers to a compound formed by the union of one or more electron-rich and electron-poor molecules or atoms capable of independent existence with one or more electronically poor molecules or atoms, each of which is also capable of independent existence. A "coordination complex" is one type of a complex, in which there is a coordinate bond between a metal ion and an electron pair donor. A transition metal complex is a coordination complex in which the metal ion is a transition metal ion. In general, the terms "compound," "composition," "agent" and the like discussed herein include complexes, coordination complexes and transition metal complexes. As a general matter, the teachings of *Advanced Inorganic Chemistry* by Cotton and Wilkinson are referenced as supplementing the definitions herein in regard to coordination complexes and related matters.

In certain circumstances, a coordination complex may be understood to be composed of its constitutive components. For example, a coordination complex may have the following components: (i) one or more metal ions, which may or may not be the same atom, have the same charge, coordination number or coordination geometry and the like; and (ii) one or more Lewis bases that form coordinate bonds with the metal ion(s). Examples of such Lewis bases include chelating agents and ligands. Examples of such chelating agents and ligands include the metal binding domains and therapeutic agents of the present invention.

If a transitional metal complex is charged, in that the transition metal ion and any Lewis bases, in the aggregate, are not neutral, then such a complex will usually have one or more counterions to form a neutral compound. Such counterions may or may not be considered part of the coordination complex depending on how the term coordination complex is used. Counterions generally do not form coordinate bonds to the metal ion, although they may be associated, often in the solid state, with the metal ion or Lewis bases that make up the coordination complex. Some examples of counterions include monoanions such as nitrate, chloride, tetrafluoroborate, hexafluorophosphate, and monocarboxylates having the general formula $RCOO^-$, and dianions such as sulfate. In some cases, coordination complexes themselves may serve as counterions to another coordination complex, as in Magnus (green) salt $[Pt(NH_3)_4]^{2+}[PtCl_4]^{2-}$.

The same chemical moiety may be either a ligand or a counterion to a coordination complex. For example, the anionic ligand chloride may be either coordinately bound to a metal ion or may act as a counterion without any need for bond formation. The exact form observed for chloride in any coordination complex will depend on a variety of factors, including theoretical considerations, such as kinetic versus thermodynamic effects, and the actual synthetic procedures utilized to make the coordination complex, such as the extent of reaction, acidity, concentration of chloride. These considerations are applicable to other counterions as well.

Additionally, a coordination complex may be solvated. Solvation refers to molecules, usually of solvent and often water, that associate with the coordination complex in the solid state. Again, as for counterions, such solvation molecules may or may not be considered part of the coordination complex depending on how the term coordination complex is used.

The term "hrGH" is art-recognized and refers to human recombinant growth hormone.

The term "tether" is art-recognized and refers to, as used herein, a chemical linking moiety between a metal ion center and another chemical moiety, often a therapeutic agent. As such, the tether may be considered part of the chemical moiety (e.g., therapeutic agent).

When used with respect to an active agent, the term "sustained release" or "released in a sustained manner" is art-recognized. For example, a subject composition which releases an active agent over time may exhibit sustained release characteristics, in contrast to a bolus type administration in which the entire amount of the active agent is made biologically available at one time. This sustained release may result in prolonged delivery of effective amounts of the particular active agent.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compounds of the present invention, such as the subject coordination complex, may be administered in a sufficient amount to produce a at a reasonable benefit/risk ratio applicable to such treatment.

The terms "combinatorial library" or "library" are art-recognized and refer to a plurality of compounds, which may be termed "members," synthesized or otherwise prepared from one or more starting materials by employing either the same or different reactants or reaction conditions at each reaction in the library. There are a number of other terms of relevance to combinatorial libraries (as well as other technologies). The term "identifier tag" is art-recognized and refers to a means for recording a step in a series of reactions used in the synthesis of a chemical library. The term "immobilized" is art-recognized and, when used with respect to a species, refers to a condition in which the species is attached to a surface with an attractive force stronger than attractive forces that are present in the intended environment of use of the surface, and that act on the species. The term "solid support" is art-recognized and refers to a material which is an insoluble matrix, and may (optionally) have a rigid or semi-rigid surface. The term "linker" is art-recognized and refers to a molecule or group of molecules connecting a support, including a solid support or polymeric support, and a combinatorial library member. The term "polymeric support" is art-recognized and refers to a soluble or insoluble polymer to which a chemical moiety can be covalently bonded by reaction with a functional group of the polymeric support. The term "functional group of a polymeric support" is art-recognized and refers to a chemical moiety of a polymeric support that can react with an chemical moiety to form a polymer-supported amino ester.

The term "synthetic" is art-recognized and refers to production by in vitro chemical or enzymatic synthesis.

The term "meso compound" is art-recognized and refers to a chemical compound which has at least two chiral centers but is achiral due to a plane or point of symmetry.

The term "chiral" is art-recognized and refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" is art-recognized and refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" is art-recognized and refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" is art-recognized and refers to molecules with identical chemical constitution and containing more than one stereocenter, but which differ in configuration at only one of these stereocenters.

The term "$ED_{50}$" is art-recognized and refers to the dose of a drug or other compound or coordination complex which produces 50% of its maximum response or effect, or alternatively, the dose which produces a pre-determined response in 50% of test subjects or preparations.

The term "$LD_{50}$" is art-recognized and refers to the dose of a drug or other compound or coordination complex which is lethal in 50% of test subjects.

The term "therapeutic index" is art-recognized and refers to the therapeutic index of a drug or other compound or coordination complex defined as $LD_{50}/ED_{50}$.

The term "agonist" is art-recognized and refers to a compound or coordination complex that mimics the action of natural transmitter or, when the natural transmitter is not known, causes changes at the receptor complex in the absence of other receptor ligands.

The term "antagonist" is art-recognized and refers to a compound or coordination complex that binds to a receptor site, but does not cause any physiological changes unless another receptor ligand is present.

The term "competitive antagonist" is art-recognized and refers to a compound or coordination complex that binds to a receptor site; its effects may be overcome by increased concentration of the agonist.

The term "partial agonist" is art-recognized and refers to a compound or coordination complex that binds to a receptor site but does not produce the maximal effect regardless of its concentration.

The term "aliphatic" is art-recognized and refers to a linear, branched, cyclic alkane, alkene, or alkyne. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2$—. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

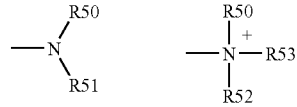

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "ammine" is art-recognized are refers to a compound containing an ammonia moiety or moieties coordinated to a metal ion. The term "ammonia" is art-recognized an refers to an amine group substituted with hydrogens.

The term "acylamino" is art-recognized and refers to a moiety that may be represented by the general formula:

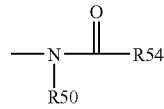

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

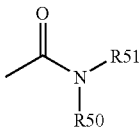

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

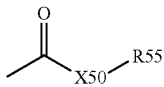 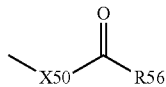

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O=(CH$_2$)$_m$—R61, where m and R61 are described above.

The term "sulfonate" is art recognized and refers to a moiety that may be represented by the general formula:

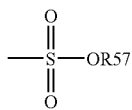

in which R57 is an electron pair, hydrogen, alkyl, cycloalkyl, or aryl.

The term "sulfate" is art recognized and includes a moiety that may be represented by the general formula:

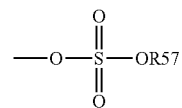

in which R57 is as defined above.

The term "sulfonamido" is art recognized and includes a moiety that may be represented by the general formula:

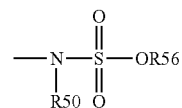

in which R50 and R56 are as defined above.

The term "sulfamoyl" is art-recognized and refers to a moiety that may be represented by the general formula:

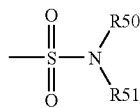

in which R50 and R51 are as defined above.

The term "sulfonyl" is art-recognized and refers to a moiety that may be represented by the general formula:

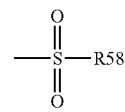

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

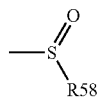

in which R58 is defined above.

The term "phosphoryl" is art-recognized and may in general be represented by the formula:

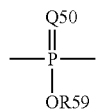

wherein Q50 represents S or O, and R59 represents hydrogen, a lower alkyl or an aryl. When used to substitute, e.g., an alkyl, the phosphoryl group of the phosphorylalkyl may be represented by the general formulas:

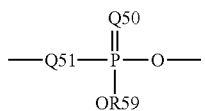 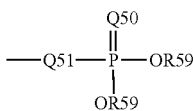

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

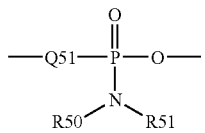 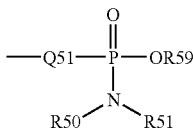

wherein Q51, R50, R51 and R59 are as defined above.

The term "phosphonamidite" is art-recognized and may be represented in the general formulas:

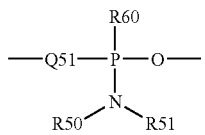 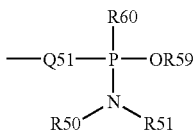

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds that may be substituted or unsubstituted.

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* ($2^{nd}$ ed., Wiley: New York, 1991).

The term "hydroxyl-protecting group" is art-recognized and refers to those groups intended to protect a hydrozyl group against undesirable reactions during synthetic procedures and includes, for example, benzyl or other suitable esters or ethers groups known in the art.

The term "carboxyl-protecting group" is art-recognized and refers to those groups intended to protect a carboxylic acid group, such as the C-terminus of an amino acid or peptide or an acidic or hydroxyl azepine ring substituent, against undesirable reactions during synthetic procedures and includes. Examples for protecting groups for carboxyl groups involve, for example, benzyl ester, cyclohexyl ester, 4-nitrobenzyl ester, t-butyl ester, 4-pyridylmethyl ester, and the like.

The term "amino-blocking group" is art-recognized and refers to a group which will prevent an amino group from participating in a reaction carried out on some other functional group, but which can be removed from the amine when desired. Such groups are discussed by in Ch. 7 of Greene and Wuts, cited above, and by Barton, *Protective Groups in Organic Chemistry* ch. 2 (McOmie, ed., Plenum Press, New York, 1973). Examples of suitable groups include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—$CH_2C_6H_5$), acyl [C(O)R1] or $SiR1_3$ where R1 is $C_1$-$C_4$ alkyl, halomethyl, or 2-halo-substituted-($C_2$-$C_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

The definition of each expression, e.g. lower alkyl, m, n, p and the like, when it occurs more than once in any structure, is intended to be independent of its definition elsewhere in the same structure.

The term "electron-withdrawing group" is art-recognized, and refers to the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, March, *Advanced Organic Chemistry* 251-59 (McGraw Hill Book Company: New York, 1977). The Hammett constant values are generally negative for electron donating groups (σ(P)=− 0.66 for $NH_2$) and positive for electron withdrawing groups (σ(P)=0.78 for a nitro group), σ(P) indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "amino acid" is art-recognized and refers to all compounds, whether natural or synthetic, which include both an amino functionality and an acid functionality, including amino acid analogs and derivatives.

The terms "amino acid residue" and "peptide residue" are art-recognized and refer to an amino acid or peptide molecule without the —OH of its carboxyl group.

The term "amino acid residue" further includes analogs, derivatives and congeners of any specific amino acid referred to herein, as well as C-terminal or N-terminal protected amino acid derivatives (e.g. modified with an N-terminal or C-terminal protecting group).

The names of the natural amino acids are abbreviated herein in accordance with the recommendations of IUPAC-IUB.

A "reversed" or "retro" peptide sequence as disclosed herein refers to that part of an overall sequence of covalently-bonded amino acid residues (or analogs or mimetics thereof) wherein the normal carboxyl-to amino direction of peptide bond formation in the amino acid backbone has been reversed such that, reading in the conventional left-to-right direction, the amino portion of the peptide bond precedes (rather than follows) the carbonyl portion. See, generally, Goodman et al. *Accounts of Chem. Res.* 12:423 (1979).

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention may be formed by utilizing an appropriate amino acid mimetic moiety to link the two adjacent portions of the sequences depicted above utilizing a reversed peptide (reversed amide) bond.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is usually (D), and the configuration of the non-reversed portion is usually (L). Opposite or mixed configurations are acceptable when appropriate to optimize a binding activity.

The term "nucleic acid" is art-recognized and refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

An "imaging agent" shall mean a composition capable of generating a detectable image upon binding with a target and shall include radionuclides (e.g., In-111, Tc-99m, I-123, I-125 F-18, Ga-67, Ga-680); for Positron Emission Tomography (PET) and Single Photon Emission Tomography (SPECT), unpair spin atoms and free radicals (e.g., Fe, lanthanides, and Gd); and contrast agents (e.g., chelated (DTPA) manganese) for Magnetic Resonance Imaging (MRI). Imaging agents are discussed in greater detail below.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

The term "modulation" is art-recognized and refers to up regulation (i.e., activation or stimulation), down regulation (i.e., inhibition or suppression) of a response, or the two in combination or apart.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal.

The term "mammal" is known in the art, and exemplary mammals include humans, primates, bovines, porcines, canines, felines, and rodents (e.g., mice and rats).

The term "bioavailable" is art-recognized and refers to a form of the subject invention that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, coordination complexes of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject supplement, composition, therapeutic or other material other than directly into the central nervous system, such that it enters the patient's system and, thus, is subject to metabolism and other like processes, for example, subcutaneous administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

Contemplated equivalents of the compounds described herein include compounds which otherwise correspond thereto, and which have the same general properties thereof (such as other coordination complexes comprising tethered therapeutic agents), wherein one or more simple variations of substituents are made which do not adversely affect the characteristics of the compounds of interest. In general, the compounds of the present invention may be prepared by the methods illustrated in the general reaction schema as, for example, described below, or by modifications thereof, using readily available starting materials, reagents and conventional synthesis procedures. In these reactions, it is also possible to make use of variants which are in themselves known, but are not mentioned here.

General Introduction

In part, the present invention relates to a carrier with a metal binding domain, a metal ion chelated to the metal binding domain, and an active agent with a metal binding domain coordinated to the metal ion. By way of a further embodiment, the carrier may contain protective side chains.

The carrier compositions of the present invention include polymers and co-polymers of linear or branched structure or conjugates thereof, micelles, emulsions, and solid surfaces, where the polymers may in addition self-organize in supramolecular structures including at least two polymers. The copolymers include as one of the main polymeric elements a backbone carrier that contains metal binding domains where said domains comprise chelating groups covalently attached to the monomeric units of the backbone element or comprised of non-modified monomeric units that are spontaneously folding with the formation of metal-binding domains.

In one example, a composition of the present invention comprises the backbone linear polyamino acid with degree of polymerization in the range of 2-10,000 to which independently and covalently linked are methoxypolyethylene glycol (mPEG) protective chains with a mass of 300-6000 D and chelating groups, where said chains and chelating groups are independently linked to the backbone. In another example, the degree of polymerization is in the range of 100-1,000. In still another example, the degree of polymerization is in the range of 100 to 300. The metal binding domains of the present invention may include polycarboxylic acids containing nitrogen where at least one of carboxylic groups may be utilized for covalent linking of the chelate to the carrier backbone polymer component of the composition of the invention. The addition of said metal ions to chelates included in the carrier compositions of the invention either at room temperature or at elevated temperatures results in the formation of coordinate complexes (metal-chelates). These metal-chelate complexes bind to the metal binding domain of peptide or protein, added either in a purified state or in the presence of bulk protein or blood plasma proteins, with the formation of drug-delivery compositions containing coordinate complexes formed between the metal-chelate and peptides or proteins. The amino acid sequence of peptides or proteins of the invention may include one or more histidines or cysteines which increase the stability of the complex formed between the peptide or protein and metal-chelate complexes bound to compositions of the invention.

For the purpose of delivery of peptides and proteins to their receptors on cells or other molecular targets in the body with the goal of providing medicinal, therapeutic, targeting or diagnostic effects, the bond between the metal-chelate and peptide or protein is chosen to allow dissociation of the peptide or protein from the metal-chelate bound to the carrier composition. The dissociation of the bond between metal-chelate and peptide or protein can be accelerated by the administration of competing compounds (histidine, imidazole).

For the purpose of stabilization and better distribution/dissolution of peptides and proteins, and other biologically active molecules in water and organic solvent(s) based environment of formulations and drug delivery systems, the described composition of association of polymer, chelate-metal, and bound peptide or protein allow significant increase in stability, solubility and distribution of the active molecule.

Carrier

The carrier of the present invention may be any substance capable of supporting at least one metal binding domain which in turn chelates a metal ion which in turn coordinates active agents. Non-limiting examples of carriers include polymers and copolymers, micelles, reverse micelles, liposomes, microspheres, emulsions, hydrogels, microparticles, nanoparticles, and solid surfaces. In one aspect, the carrier is biocompatible.

(i) Polymers and Co-polymers

In certain embodiments, the polymers or co-polymers of the subject compositions, e.g., which include repetitive elements shown in any of the subject formulas, have molecular weights ranging from about 2000 or less to about 1,000,000 or more daltons, or alternatively about 10,000, 20,000, 30,000, 40,000, or 50,000 daltons, more particularly at least about 100,000 daltons, and even more specifically at least about 250,000 daltons or even at least 500,000 daltons. Number-average molecular weight (Mn) may also vary widely, but generally fall in the range of about 1,000 to about 200,000 daltons, or even from about 1,000 to about 100,000 daltons or even from about 1,000 to about 50,000 daltons. In one embodiment, Mn varies between about 8,000 and 45,000 daltons. Within a given sample of a subject polymer, a wide range of molecular weights may be present. For example, molecules within the sample may have molecular weights which differ by a factor of 2, 5, 10, 20, 50, 100, or more, or which differ from the average molecular weight by a factor of 2, 5, 10, 20, 50, 100, or more.

One method to determine molecular weight is by gel permeation chromatography ("GPC"), e.g., mixed bed columns, $CH_2Cl_2$ solvent, light scattering detector, and off-line dn/dc. Other methods are known in the art.

In certain embodiments, the intrinsic viscosities of the polymers generally vary from about 0.01 to about 2.0 dL/g in chloroform at 40° C., alternatively from about 0.01 to about 1.0 dL/g and, occasionally, from about 0.01 to about 0.5 dL/g.

The glass transition temperature (Tg) of the subject polymers may vary widely, and depend on a variety of factors, such as the degree of branching in the polymer components, the relative proportion of phosphorous-containing monomer used to make the polymer, and the like. When the article of the invention is a rigid solid, the Tg is often within the range of from about −10° C. to about 80° C., particularly between about 0 and 50° C. and, even more particularly between about 25° C. to about 35° C. In other embodiments, the Tg is low enough to keep the composition of the invention flowable at body temperature. Then, the glass transition temperature of the polymer used in the invention is usually about 0 to about 37° C., or alternatively from about 0 to about 25° C.

In other embodiments, the polymer composition of the invention may be a flexible or flowable material. When the polymer used is itself flowable, the polymer composition of the invention, even when viscous, need not include a biocompatible solvent to be flowable, although trace or residual amounts of biocompatible solvents may still be present.

A flexible polymer may be used in the fabrication of a solid article. Flexibility involves having the capacity to be repeatedly bent and restored to its original shape. Solid articles made from flexible polymers are adapted for placement in anatomic areas where they will encounter the motion of adjacent organs or body walls. A flexible solid article can thus be sufficiently deformed by those moving tissues that it does not cause tissue damage. Flexibility is particularly advantageous where a solid article might be dislodged from its original position and thereby encounter an unanticipated moving structure; flexibility may allow the solid article to bend out of the way of the moving structure instead of injuring it. Such a flexible article might be suitable for covering pulsatile vessels such as the carotid artery in the neck, or for covering more delicate structures in the neck like the jugular vein that may also be affected by local movements. Similarly, a flexible solid article may be used to protect nerves exposed during a neck dissection such as the spinal accessory nerve, wherein the flexibility of the solid article may permit it to bend or deform when encountering motion rather than eroding into or damaging the nerve. Use of a solid carrier according to the present invention in the aforesaid ways may allow less extensive dissections to be carried out with surgical preservation of structures important to function. Solid articles may be configured as three-dimensional structures suitable for implantation in specific anatomic areas. Solid articles may be formed as films, meshes, sheets, tubes, or any other shape appropriate to the dimensions and functional requirements of the particular anatomic area. Physical properties of polymers may be adjusted to attain a desirable degree of flexibility by modification of the chemical components and crosslinking thereof, using methods familiar to practitioners of ordinary skill in the art.

Examples of polymeric carriers include carboxylated or carboxymethylated linear poly-1-lysine (PL) or poly-D-lysine; carboxylated or carboxymethylated poly-alfa,beta-(2-aminoethyl)-D,L-aspartamide; poly-1-aspartic acid; poly-glutamic acid, copolymers of histidine with positively or negatively charged aminoacids, carboxylated polyethyleneimines, i.e. polyethylene imines reacted with derivatives of carbonic acids; natural saccharides or products chemically derived thereof, bearing carboxylic groups, which may be exemplified by: galacturonic acid, glucuronic acid, mannuronic acid, hyaluronic acid, pectic acid, neuraminic acid, alginic acid, carrageenan; oxidized dextrans; aminated, e.g. containing linked aminogroups, polysaccharides or oligosaccharides, linear or branched; carboxylated, carboxymethylated, sulfated or phosphorylated polysaccharides or oligosaccharides, e.g. reacted with derivatives of carbonic, dicarbonic, sulfuric, aminosulfuric, phosphoric acids with resultant linking of carboxylic, aminocarboxylic, carboxymethyl, sulfuric, amino or phosphate groups. Such olygosaccharides may be obtained by chemical alteration of, e.g., dextran, mannan, xylan, pullulan, cellulose, chytosan, agarose, fucoidan, galactan, arabinan, fructan, fucan, chitin, pustulan, levan or pectin. In addition these poly- or oligosaccharides may be represented by heteropolymers or homopolymers of monosaccharides such as glucose, galactose, mannose, galactose, deoxyglucose, ribose, deoxyribose, arabinose, fucose, xylose, xylulose, ribulose, polyamidoamine, linear or branched; polyacrylic acid; polyalcohols, e.g. polyvinylalcohol an polyxylitol, to which carboxylic or aminogroups are chemically linked. The molecular weight of a polyaminoacid is preferably larger than 1000 and smaller than 100000. Polyamino acids with narrow molecular weight (MW) distribution are preferred to those with broad MW distribution. Polyamino acids are linked with peptide bonds. Polyaminoacids are prepared by chemical synthesis or by recombinant techniques, such as genetic engineering. For additional examples of polymers suitable for use in the present invention see U.S. Pat. Nos. 6,509,323; 6,492,560; 6,468,532; 6,521,736; 6,348,069; 5,871,710; and 6,051,549. In another embodiment, the polymer acting as the carrier may be poly(ethylene glycol) (PEG) with functional groups at the far-end making up the metal binding domain to which the metal ion coordinates and in turn coordinates the active agent. Schematically the embodiment may be represented by the following: PEG-MBD-Metal-MBD-Active agent. Alternatively, PEG may be functionalized along its backbone allowing MBD-Metal-MBD-Active agent moieties to be pendant to the backbone. This functionalization may also allow pendant protective chains as well.

(ii) Micelles, Reverse Micelles, Liposomes and Microspheres

Amphipathic compounds that contain both hydrophobic and hydrophilic domains are typically organized into vesicular structures such as liposomes, micellar, or reverse micellar structures. Liposomes can contain an aqueous volume that is entirely enclosed by a membrane composed of lipid molecules (usually phospholipids). Micelles and reverse micelles are microscopic vesicles that contain amphipathic molecules but do not contain an aqueous volume that is entirely enclosed by a membrane. In micelles the hydrophilic part of the amphipathic compound is on the outside (on the surface of the vesicle) whereas in reverse micelles the hydrophobic part of the amphipathic compound is on the outside. The reverse micelles thus contain a polar core that can solubilize both water and macromolecules within the inverse micelle. As the volume of the core aqueous pool increases the aqueous environment begins to match the physical and chemical characteristics of bulk water. The resulting inverse micelle can be referred to as a microemulsion of water in oil.

In water, when a sufficient concentration of the two or more components that make up a micelle is present, the components spontaneously aggregate into thermodynamically stable polymeric micelles. The micelle particles assume a microspheroidal shape and possess, in essence, a double layer. The core "layer" forms by virtue of the hydrophobic interactions between, for example, hydrophobic polyesters. Similarly, the surface "layer" forms by virtue of the corresponding hydrophilic interactions of a, for example, hydrophilic polycation with water. A net positive charge will exist around the surface of the micelle, since the hydrophilic segment of the first component is a polycation.

Functional compounds having metal binding properties can be easily introduced to the micelle by: (1) creating a third copolymer component that bears the functional group and (2) coupling the copolymer to the surface of a pre-assembled polymeric micelle. Alternatively, a metal binding domain-bearing component can be incorporated into a micelle at the time the micelle originally forms. If so, then it may be preferable to use a copolymer wherein the metal binding domain resides in the hydrophilic segment so that it is exposed in the micelle surface layer. It is an advantage of the present invention that the kind and content of the functional group can be easily changed without limitation.

Micelles according to the present invention may comprise biodegradable, biocompatible copolymers, resulting in non-immunogenicity and non-toxicity. In one aspect copolymers disclosed herein degrade into non-toxic, small molecules subject to renal excretion and are inert during the required period of treatment. Degradation may occur via simple hydrolytic and/or enzymatic reaction. Degradation through simple hydrolysis may be predominant when the backbone of a copolymer comprises ester bonds. Enzymatic degradation may become significant in the presence of certain organelles such as lyposomes. The degradation period can be varied from days to months by using polymers of different kinds and molecular weights. In one example, the present invention may use biodegradable polyesters or polypeptides possessing safe and biocompatible degradation pathways. In addition, the highly-branched micellar structure of the present invention may further reduce cytotoxicity since branched polycations such as dendritic polyamidoamines are thought to be less cytotoxic than linear polycations. Accordingly, the advantageous components and structure of polymeric micelles according to the present invention can be appreciated regarding reduced cytotoxicity. For additional examples of micelles, reverse micelles, liposomes, and microspheres suitable for the present invention see U.S. Pat. Nos. 6,338,859, 5,631,018; 6,162,462; 6,475,779; 6,521,211; and 6,443,898.

(iii) Emulsions and Hydrogels

Emulsions as the carrier in the present invention relate to emulsions of an aqueous or an aqueous-organic continuous phase and an organic discontinuous phase, the latter containing an organic solvent which is not miscible with water. Hydrogels are similar and refer to a type of gel in which the disperse phase has combined with water to produce a semi-solid material. The emulsions and hydrogels used in the present invention may contain organic compounds from the group of the reaction products of alkylene oxides with compounds capable of being alkylated, such as, for example, fatty alcohols, fatty amines, fatty acids, phenols, alkylphenols, carboximides and resinic acids, preferably balsamic resin and/or abietic acid.

Organic solvents which are not miscible with water include, for example, aliphatic, cycloaliphatic or aromatic hydrocarbons or the acetate-type solvents. Suitable as organic solvents are, preferably, natural, fully- or semisynthetic compounds and, if appropriate, mixtures of these solvents which are fully miscible or soluble with the other compounds of the emulsion in the temperature range of from 20 to 130° C. In one embodiment, suitable solvents are those from the group of the aliphatic, cycloaliphatic or aromatic hydrocarbons which are liquid at room temperature, including oils, such as, for example, mineral oils, paraffins, isoparaffins, fully-synthetic oils such as silicon oils, semisynthetic oils based on, for example, glycerides of unsaturated fatty acids of medium chain length, essential oils, esters of natural or synthetic, saturated or unsaturated fatty acids, for example $C_8$-$C_{22}$-fatty acids, $C_8$-$C_{18}$-fatty acids, especially preferably methyl esters of rapeseed oil or 2-ethylhexyl laurate, alkylated aromatics and their mixtures, alkylated alcohols, in particular fatty alcohols, linear, primary alcohols obtained by hydroformylation, terpene hydrocarbons and naphtene-type oils, such as, for example, Enerthene. Further organic solvents include those from the group of the acetate-type solvents such as, for example, 1,2-propanediol diacetate, 3-methyl-3-methoxybutyl acetate, ethyl acetate and the like. The solvents can be employed individually or as mixtures with each other.

The continuous aqueous or aqueous-organic phase of the active-agent-containing emulsions or microemulsions according to the present invention contain water, an organic solvent that is soluble or miscible in water, and may also contain at least one natural or synthetic surface-active agent which has a solubility of >10 g/l, in particular >100 g/l in water (d) at 20° C., and, if appropriate, further adjuvants. Organic solvents which are soluble or miscible in water have a solubility in water of >5.0 g/l at 20° C., in particular >15 g/l.

Examples of suitable organic solvents are: aliphatic $C_1$-$C_4$-alcohols such as methanol, ethanol, isopropanol, n-propanol, n-butanol, isobutanol or tert-butanol, aliphatic ketones such as acetone, methyl ethyl ketone, methyl isobutyl ketone or diacetone alcohol, polyols, such as ethylene glycol, propylene glycol, butylene glycol, 1,4-butanediol, 1,5-pentanediol, 1,6-hexanediol, diethylene glycol, triethylene glycol, trimethylolpropane, polyethylene glycol or polypropylene glycol with a mean gram-molecular weight of 100 to 4000 g/mol or 200 to 1500 g/mol, or glycerol, monohydroxyethers, such as monohydroxyalkyl ethers or mono-$C_1$-$C_4$-alkyl glycol ethers such as ethylene glycol monoethyl ether, ethylene glycol monomethyl ether, diethylene glycol monomethyl ether or diethylene glycolmonoethyl ether, diethylene glycol monobutyl ether, dipropylene glycol monoethyl ether, thiodiglycol, triethylene glycol monomethyl ether or triethylene glycol monoethyl ether, furthermore 2-pyrrolidone, N-methyl-2-pyrrolidone, N-ethyl-pyrrolidone, N-vinylpyrrolidone, 1,3-dimethylimidazolidone, dimethylacetamide and dimethyl formamide.

The amount of the solvents employed in the aqueous continuous phase is in general less than 60% by weight or less than 40% by weight, based on the continuous phase.

Surface-active agents are understood as meaning emulsifiers, wetters, dispersants, antifoams or solubilizers which are soluble or fully soluble, in the aqueous phase. In particular, they can be nonionic, anionic, cationic or amphoteric or of monomeric, oligomeric or polymeric nature. The choice of the surface-active agents is not limited in accordance with the present invention and must be matched with the discontinuous phase to be stabilized with regard to the desired type of emulsion (for example miniemulsion or microemulsion) and the stability of the emulsion, in particular the sedimentation and/or creaming of the disperse phase.

Examples of suitable surface-active agents include the following: a) alkoxylation product which can be obtained by ethylene-oxide-alkoxylation or propylene-oxide-alkoxylation of condensates of phenolic OH-containing aromatics with formaldehyde and NH functional groups; b) inorganic salts which are soluble in water, such as borates, carbonates, silicates, sulfates, sulfites, selenates, chlorides, fluorides, phosphates, nitrates and aluminates of the alkali metals and alkaline earth metals and other metals and also ammonium; c) polymers composed of recurrent succinyl units, in particular polyaspartic acid; d) nonionic or ionically modified compounds form the group of the alkoxylates, alkylolamides, esters, amine oxides and alkyl polyglycosides, including reaction products of alkylene oxides with compounds capable of being alkylated, such as, for example, fatty alcohols, fatty amines, fatty acids, phenols, alkyl phenols, carboximides and resinic acids. These are, for example, ethylene oxide adducts from a class of the reaction products of ethylene oxide with: 1) saturated and/or unsaturated fatty alcohols with 6 to 25 C atoms or 2) alkyl phenols with 4 to 12 C atoms in the alkyl radical or 3) saturated and/or unsaturated fatty amines with 14 to 20 C atoms or 4) saturated and/or unsaturated fatty acids with 14 to 22 C atoms or 5) hydrogenated and/or unhydrogenated resinic acids, or 6) esterification and/or arylation products prepared from natural or modified, optionally hydrogenated castor oil lipid bodies which, if appropriate, are linked by esterification with dicarboxylic acids to give recurrent structural units; e) ionic or nonionic compounds from the group of the reaction products of alkylene oxide with sorbitan ester, oxalkylated acetylene diols and acetylene glycols, and oxalkylated phenols; f) ionic or nonionic polymeric surface-active agents from the group of the homo- and copolymers, graft and graft copolymers and random and linear block copolymers. Examples of such suitable polymeric surface-active agents include polyethylene oxides, polypropylene oxides, polyoxymethylenes, polytrimethylene oxides, polyvinyl methyl ethers, polyethylene imines, polyacrylic acid, polyaryl amides, polymethacrylic acids, polymethacrylamides, poly-N,N-dimethyl-acrylamides, poly-N-isopropyl acrylamides, poly-N-acrylglycinamides, poly-N-methacrylglycinamides, polyvinyloxazolidones, polyvinylmethyloxazolidones; g) anionic surface-active agents such as, for example, alkyl sulfates, ether sulfates, ether carboxylates, phosphate esters, sulfosuccinate amides, paraffin sulfonates, olefin sulfonates, sarcosinates, isothionates and taurates; h) anionic surface-active agents from the group of what is known as dispersants, in particular condensates which can be obtained by reacting naphthols with alkanols, subjecting alkylene oxide to an addition reaction and at least partially converting the terminal hydroxyl groups into sulfo groups or monoesters of maleic acid, phthalic acid or succinic acid, sulfosuccinic esters, alkylbenzene sulfonates, and salts of the polyacrylic acids, polyethylene sulfonic acids, polystyrene sulfonic acid, polymethacrylic acids, polyphosphoric acids; i) lignin-type compounds, especially lignosulfonates, for example those which have been obtained by the sulfite or Kraft method. They include products which are partially hydrolyzed, oxidized, propoxylated, sulfonated, sulfomethylated or bisulfonated and which are fractionated by known methods, for example according to the molecular weight or the degree of sulfonation. Mixtures of sulfite and Kraft lignosulfonates are also very effective. Suitable are lignosulfonates with a mean molecular weight of greater than about 1,000 to 100,000, a content of active lignosulfonate of at least 80% and, a low content of polyvalent cations. The degree of sulfonation can be varied within wide limits.

In another embodiment, the continuous aqueous phase can also contain, in addition to the abovementioned surface-active agents, water-soluble block or block copolymers; these block or block copolymers include water-soluble block and block copolymers based on ethylene oxide and/or propylene oxide and/or water-soluble block and block copolymers of ethylene oxide and/or propylene oxide on bifunctional amines. Block copolymers based on polystyrene and polyalkylene oxide, poly(meth)acrylates and polyalkylene oxide and also poly(meth)acrylates and poly(meth)acrylic acids are also suitable.

In addition, the continuous aqueous phase can also contain further customary adjuvants such as, for example, water-soluble wetters, antifoams and/or preservatives.

Emulsion types of the present invention which may be mentioned are: macroemulsion: contains droplets >2 μm (microscopic); miniemulsion: droplet diameter 0.1 to 2 μm, turbid; and microemulsion: droplet diameter <0.1 μm; transparent. For additional examples of emulstions and hydrogels suitable for the present invention see U.S. Pat. Nos. 6,458,373 and 6,124,273.

(iv) Nanoparticles and Microparticles

Examples of nanoparticles and microparticles that can be used as a carrier in the present invention are include porous particles having a mass density less than 1.0 $g/cm^3$, or less than about 0.4 $g/cm^3$. The porous structure permits, for example, deep lung delivery of relatively large diameter therapeutic aerosols, for example greater than 5 μm in mean diameter.

The porous particles preferably are biodegradable and biocompatible, and optionally are capable of biodegrading at a controlled rate for delivery of a drug. The porous particles may be made of any material which is capable of forming a porous particle having a mass density less than about 0.4 g/cm$^3$. Both inorganic and organic materials can be used. For example, ceramics may be used. Other non-polymeric materials may be used which are capable of forming porous particles as defined herein.

The particles may be formed from any biocompatible, and preferably biodegradable polymer, copolymer, or blend, which is capable of forming porous particles having a density less than about 0.4 g/cm$^3$.

Surface eroding polymers such as polyanhydrides may be used to form the porous particles. For example, polyanhydrides such as poly[(p-carboxyphenoxy)-hexane anhydride] ("PCPH") may be used. Biodegradable polyanhydrides are described, for example, in U.S. Pat. No. 4,857,311.

In another embodiment, bulk eroding polymers such as those based on polyesters including poly(hydroxy acids) can be used. For example, polyglycolic acid ("PGA") or polylactic acid ("PLA") or copolymers thereof may be used to form the porous particles, wherein the polyester has incorporated therein a charged or functionalizable group such as an amino acid as described below.

Other polymers include polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses, polysaccharides, and peptides or proteins, or copolymers or blends thereof which are capable of forming porous particles with a mass density less than about 0.4 g/cm$^3$. Polymers may be selected with or modified to have the appropriate stability and degradation rates in vivo for different controlled drug delivery applications.

As another example, the porous particles may be formed from functionalized polyester graft coppolymers, as described in Hrkach et al., Macromolecules, 28:4736-4739 (1995); and Hrkach et al., "Poly(L-Lactic acid-co-amino acid) Graft Copolymers: A Class of Functional Biodegradable Biomaterials" in Hydrogel and Biodegradable Polymers for Bioapplications, ACS Symposium Series No. 627, Raphael M. Ottenbrite et al., Eds., American Chemical Society, Chapter 8, pp. 93-101, 1996, the disclosures of which are incorporated herein by reference. The functionalized graft copolymers are copolymers of polyesters, such as poly(glycolic acid) or poly(lactic acid), and another polymer including functionalizable or ionizable groups, such as a poly (amino acid). In another embodiment, comb-like graft copolymers are used which include a linear polyester backbone having amino acids incorporated therein, and poly (amino acid) side chains which extend from the amino acid groups in the polyester backbone. The polyesters may be polymers of α-hydroxy acids such as lactic acid, glycolic acid, hydroxybutyric acid and valeric acid, or derivatives or combinations thereof. The inclusion of ionizable side chains, such as polylysine, in the polymer has been found to enable the formation of more highly porous particles, using techniques for making microparticles known in the art, such as solvent evaporation. Other ionizable groups, such as amino or carboxyl groups, may be incorporated, covalently or noncovalently, into the polymer to enhance porosity. For example, polyaniline could be incorporated into the polymer.

An exemplary polyester graft copolymer, which may be used to form porous polymeric particles is the graft copolymer, poly(lactic acid-co-lysine-graft-lysine) ("PLAL-Lys"), which has a polyester backbone consisting of poly(L-lactic acid-co-Z-L-lysine) (PLAL), and grafted lysine chains. PLAL-Lys is a comb-like graft copolymer having a backbone composition, for example, of 98 mol % lactic acid and 2 mol % lysine and poly(lysine) side chains extending from the lysine sites of the backbone.

The use of the poly(lactic acid) copolymer is advantageous since it biodegrades into lactic acid and lysine, which can be processed by the body. The existing backbone lysine groups are used as initiating sites for the growth of poly(amino acid) side chains.

In the synthesis, the graft copolymers may be tailored to optimize different characteristic of the porous particle including: i) interactions between the agent to be delivered and the copolymer to provide stabilization of the agent and retention of activity upon delivery; ii) rate of polymer degradation and, thereby, rate of drug release profiles; iii) surface characteristics and targeting capabilities via chemical modification; and iv) particle porosity. For additional examples of nanoparticles and microparticles suitable for the present invention see U.S. Pat. Nos. 6,447,753 and 6,274,175.

(v) Solid Surface

In certain embodiments, the carrier used in the present invention may be a solid support, e.g., a polymer bead or a resin, e.g., a Wang resin. Supports can be solids having a degree of rigidity such as silicon, plastic, and the like. Support can also be flexible materials such as plastic or otherwise synthetic materials (such as nylon), materials made of natural polymers (such as cellulose or silk) or derivatives thereof (such as nitrocellulose) and the like. In certain embodiments the support is a porous material which can be rigid or flexible, intermeshed fibers including woven fabrics, and the like. In some embodiments, the solid support is a bead or pellet, which can be porous.

Another option for creating a solid support with reactive sites is to directly derivatize the solid support so that it can be coupled to a compound. The chemistry used to do this can be the same or similar to that used to derivatize controlled pore glass (cpg) beads and polymer beads. Typically, the first step in this process is to create hydroxyl groups (if they do not already exist on the support) or amino groups on the support. If hydroxyl groups exist or are created, they are typically converted to amino groups, for instance by reacting them with gamma-aminopropyl triethoxy silane. MBDs can be added to the amino groups with cyclic acid anhydrides, activated esters, reactions with polymerized alkylene oxides and other methods known to the art.

Another method to increase the reactive surface area of a solid support is to create columnar structures of silicon monoxide, for instance by thermal evaporation of $SiO_x$. Another such method is to insert into the reaction cells fabrics, such as non-woven glass or plastic (preferably fiberglass or polypropylene fiber) fabrics and plasma treating the fabric to create reactive sites. Still another method uses spin-on glass, which creates a thin film of nearly stoichiometric $SiO_2$ from a silsesquioxane ladder polymer structure by thermal oxidation. Sol-gel processing creates thin films of glass-like composition from organometallic starting materials by first forming a polymeric organometallic structure in mixed alcohol plus water and then careful drying and baking. When the sol-gel system is dried above the critical temperature and pressure of the solution, an aerogel results. Aerogels have chemical compositions that are similar to glasses (e.g. $SiO_2$) but have extremely porous microstructures. Their densities are comparably low, in some cases having only about one to about three percent solid composition, the balance being air.

Protective Side Chains

Examples of Protective Chains include poly(ethylene glycol), which may be esterified by dicarboxylic acid to form a poly(ethylene glycol) monoester; methoxy poly(ethylene glycol) (MPEG) or a copolymer of poly(ethylene glycol) and poly(propylene glycol) preferably in a form of an ester with dicarboxylic acid; poly(ethylene glycol)-diacid; poly(ethylene glycol) monoamine; methoxy poly(ethylene glycol) monoamine; methoxy poly(ethylene glycol) hydrazide; methoxy poly(ethylene glycol) imidazolide block-copolymer of poly (ethylene glycol) and one or several polymers represented by polyaminoacid, poly-lactide-glycolide co-polymer, polysaccharide, polyamidoamine, polyethyleneimine or polynucleotide (see polymeric carrier) where these blocks are preferably alternated to give a preferably linear block-copolymer. Overall molecular weight of a protective chain is preferentially larger than 300 but preferably not exceeding 10,000. A protective chain or chains are linked to the polymeric carrier by preferably a single linkage.

Metal Binding Domain

In general, the metal binding domains used in the present invention contain a Lewis base fragment that is contemplated to encompass numerous chemical moieties having a variety of structural, chemical and other characteristics capable of forming coordination bonds with a metal ion. The types of functional groups capable of forming coordinate complexes with metal ions are too numerous to categorize here, and are known to those of skill in the art. For example, such moieties will generally include functional groups capable of interaction with a metal center, e.g., heteroatoms such as nitrogen, oxygen, sulfur, and phosphorus.

Metal cations are almost always Lewis acidic and are therefore able to bind various moieties that may serve as Lewis bases. In general, a moiety serving as a Lewis base will be a strongly acidic group, e.g., with a pKa less than about 7, and more preferably less than 5, which may produce a conjugate base that, under the appropriate conditions, is a strong enough Lewis base to donate an electron pair to a metal ion to form a coordinate bond. The degree of this Lewis acid-to-Lewis base interaction is a function not only of the particular metal ion, but also of the coordinating moiety itself, because the latter may vary in the degree of basicity as well as in size and steric accessibility.

Exemplary Lewis basic moieties which may be included in the metal binding domain include: amines (primary, secondary, and tertiary) and aromatic amines, amino groups, amido groups, nitro groups, nitroso groups, amino alcohols, nitriles, imino groups, isonitriles, cyanates, isocyanates, phosphates, phosphonates, phosphites, phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls and sulfinyls.

Illustrative of suitable metal binding domains include those chemical moieties containing at least one Lewis basic nitrogen, sulfur, phosphorous or oxygen atom or a combination of such nitrogen, sulfur, phosphorous and oxygen atoms. The carbon atoms of such moiety may be part of an aliphatic, cycloaliphatic or aromatic moiety. In addition to the organic Lewis base functionality, such moieties may also contain other atoms and/or groups as substituents, such as alkyl, aryl and halogen substituents.

Further examples of Lewis base functionalities suitable for use in the metal binding domains include the following chemical moieties: amines, particularly alkylamines and arylamines, including methylamine, diphenylamine, trimethylamine, triethylamine, N,N-dimethylaniline, methyldiphenylaniline, pyridine, aniline, morpholine, N-methylmorpholine, pyrrolidine, N-methylpyrrolidine, piperidine, N-methylpiperidine, cyclohexylamine, n-butylamine, dimethyloxazoline, imidazole, N-methylimidazole, N,N-dimethylethanolamine, N,N-diethylethanolimine, N,N-dipropylethanolamine, N,N-dibutylethanolamine, N,N-dimethylisopropanolamine, N,N-diethylisopropanolamine, N,N-dipropylisopropanolamine, N,N-dibutylisopropanolamine, N-methyldiethanolamine, N-ethyldiethanolamine, N-propyldiethanolamine, N-butyldiethanolamine, N-methyldiisopropanolamine, N-ethyldiisopropanolamine, N-propyldiisopropanolamine, N-butyldiisopropanolamine, triethylamine, triisopropanolamine, tri-s-butanolamine and the like; amides, such as N,N-dimethylformamide, N,N-dimethylacetamide, N-methylpyrrolidone, hexamethylphosphoric acid triamide and the like; sulfoxide compounds, such as dimethylsulfoxide and the like; ethers such as dimethyl ether, diethyl ether, tetrahydrofuran, dioxane and the like; thioethers such as dimethylsulfide, diethyl thioether, tetrahydrothiophene and the like; esters of phosphoric acid, such as trimethyl phosphate, triethylphosphate, tributyl phosphate and the like; esters of boric acid, such as trimethyl borate and the like; esters of carboxylic acids, such as ethyl acetate, butyl acetate, ethyl benzoate and the like; esters of carbonic acid, such as ethylene carbonate and the like; phosphines including di- and trialkylphosphines, such as tributylphosphine, triethylphosphine, triphenylphosphine, diphenylphosphine and the like; and monohydroxylic and polyhydroxylicalcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-pentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like; and heterocyclic compounds, including pyridine and the like.

Other suitable structural moieties that may be included in the metal binding domains include the following Lewis base functionalities: arsine, stilbines, thioethers, selenoethers, teluroethers, thioketones, imines, phosphinimine, pyridines, pyrazoles, imidazoles, furans, oxazoles, oxazolines, thiophenes, thiazoles, isoxazoles, isothrazoles, amides, alkoxy, aryoxy, selenol, tellurol, siloxy, pyrazoylborates, carboxylate, acyl, amidates, triflates, thiocarboxylate and the like.

Other suitable ligand fragments for use in the metal binding domains include structural moieties that are bidentate ligands, including diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

Still other suitable fragments for use in the metal binding domains include ligand fragments that are tridentate ligands, including 2,5-diiminopyridyl ligands, tripyridyl moieties, triimidazoyl moieties, tris pyrazoyl moieties, and combinations of the above ligands.

Other suitable ligand fragments may consist of amino acids or be formed of oligopeptides and the like.

Because the Lewis basic groups function as the coordination site or sites for the metal cation, in certain embodiments, it may be preferable that the deformability of the electron shells of the Lewis basic groups and the metal cations be approximately similar. Such a relationship often results in a more stable coordination bond. For instance, sulfur groups may be desirable as the Lewis basic groups when the metal cation is a heavy metal. Some examples include the oligopeptides such as glutathione and cysteine, mercapto ethanol amine, dithiothreitol, amines and peptides containing sulfur and the like. Nitrogen containing groups may be employed as the Lewis basic groups when smaller metal ions are the metal. Alternatively, for those applications in which a less stable coordination bond is desired, it may be desirable that the deformability be dissimilar.

Further examples of chelating groups which act as the metal binding domain and can be chemically linked the carrier include 1,4,7,10-tetraazacyclododecane-N,N',N'',N'''-tetraacetic acid; 1,4,7,10-tetraaza-cyclododecane-N,N',N''-triacetic acid; 1,4,7-tris(carboxymethyl)-10-(2'-hydroxypropyl)-1,4,7,10-tetraazocyclodecane, 1,4,7-triazacyclonane-N,N',N''-triacetic acid; and 1,4,8,11-tetraazacyclotetra-decane-N,N',N'',N'''-tetraacetic acid; diethylenetriamine-pentaacetic acid (DTPA); triethylenetetraamine-hexaacetic acid; ethylenediamine-tetraacetic acid (EDTA); EGTA; 1,2-diaminocyclohexane-N,N,N',N'-tetraacetic acid but preferably N-(hydroxyethyl)ethylenediaminetriacetic acid; nitrilotriacetic acid (NTA); and ethylenebis(oxyethylene-nitrilo)tetraacetic acid, histidine, cysteine, oligoaspartic acid, oligoglutamic acid, S-acetyl mercaptoacetate and meractoacetyltriglycine.

Metal Ion

The present invention contemplates the use of a variety of different metal ions. The metal ion may be selected from those that have usually two, three, four, five, six, seven or more coordination sites. A non-limiting list of metal ions for which the present invention may be employed (including exemplary and non-limiting oxidation states for them) includes $Co^{3+}$, $Cr^{3+}$, $Hg^{2+}$, $Pd^{2+}$, $Pt^{2+}$, $Pd^{4+}$, $Pt^{4+}$, $Rh^{3+}$, $Ir^{3+}$, $Ru^{3+}$, $Co^{2+}$, $Ni^{2+}$, $Cu^{2+}$, $Zn^{2+}$, $Cd^{2+}$, $Pb^{2+}$, $Mn^{2+}$, $Fe^{3+}$, $Fe^{2+}$, Tc, $Au^{3+}$, $Au^+$, $Ag^+$, $Cu^+$, $MoO_2^{2+}$, $Ti^{3+}$, $Ti^{4+}$, $CH_3Hg^+$, and $Y^{+3}$. In another embodiment, the non-limiting list of metal ions for which the present invention may be employed includes $Zn^{2+}$, $Ni^{2+}$, $Co^{2+}$, $Fe^{2+}$, $Mn^{2+}$, and $Cu^{2+}$. The metal ion contained in the metal bridge between the carrier and the active agent may have a therapeutic use itself, but it cannot serve as the active agent.

Active Agent

Active agents of the present invention are envisioned to be any compound possessing beneficial health properties and a metal binding domain capable of coordinating to the metal ion, thus completing a bridge between the active agent and the carrier. Non-limiting examples of active agents include, for example, diagnostics, targeting moieties, antigens, and therapeutic agents.

(i) Diagnostics

It is envisioned that the present invention can utilize any chemical moiety capable of acting as a diagnostic type of active agent. One example of such a chemical moiety is provided by radionuclides, which may then be detected using positron mission tomography (PET) or single photon emission computed tomography (SPECT) imaging or other methods known to one of skill in the art. In one embodiment, the composition of the present invention comprises one of the following radionuclides: $^{131}I$, $^{125}I$, $^{123}I$, $^{99m}Tc$, $^{18}F$, $^{68}Ga$, $^{67}Ga$, $^{72}As$, $^{89}Zr$, $^{64}Cu$, $^{62}Cu$, $^{111}In$, $^{203}Pb$, $^{198}Hg$, $^{11}C$, $^{97}Ru$, and $^{201}Tl$ or a paramagnetic contrast agent, such as gadolinium, cobalt, nickel, manganese and iron. Such moieties may be chelated to their own metal binding domain which in turn would be coordinated to the metal ion found in the bridge to the carrier.

(ii) Targeting Moieties

The role of a targeting moiety is to place the compositions of the present invention in close proximity to a target within a patient's body. In this manner, it is envisioned that the present invention can utilize more than one type of active agent. For instance, one type of active agent could be a targeting moiety while another type of active agent could be a diagnostic label or therapeutic agent. Conceivably, three types of active agents could be coordinated to the carrier through a metal ion bridge.

Examples of targeting moieties include: (i) cells including smooth muscle cells, leukocytes, B-lymphocytes, T-lymphocytes, monocytes, macrophages, foam cells, platelets, granulocytes, neutophilis, heme, porphoryns, and phthalocyanines; (ii) chemotactic proteins and peptides including monocyte chemotactic protein 1 (MCP-1), N-formyl-methionyl-leucyl-phenalanine; (iii) colony stimulating factors including GM-CSF, CSF-1, and receptors and antibodies thereto; and platelet factor 4; (iv) growth factors including TGF-β and VEGF; (v) adhesive cell-surface glycoproteins including E-selectin, VCAM-1, and VCAM1β; (vi) carbohydrates including $^{11}C$-deoxy-D-glucose, and $^{18}F$-2-fluorodeoxy-D-glucose; (vii) components of a vascular inflammatory response including C1, C1q, C1r, C1s, C2, C3, C3a, C3b, C4, C4C2, C4C2C3b, C5a, C5b and C5a; (viii) interleukins including IL-1, IL-1α, IL-1β, IL-2, IL-3, IL-6, IL-7, and IL-8; (ix) interferons including interferon α and interferon γ; (x) tumor necrosis factor TNF-α; and (xi) lipids including liposomes, polyethylene glycol coated liposomes, cholesterol, esters of cholesterol, lipoproteins including LDL, HDL, oxidized LDL, and lipid receptors.

(iii) Antigens

Antigens are substances, e.g., molecules, which induce an immune response. It thus can refer to any molecule contacted by the immune system, and may include without limitation, proteins, nucleic acids and the like. Each antigen typically comprises one or more epitopes. An epitope is used to identify one or more portions of an antigen or an immunogen which is recognized or recognizable by antibodies or other immune system components.

(iv) Therapeutic Agent

As with all the active agents envisioned by the present invention, the therapeutic agent contains a metal binding domain capable of coordinating to the metal ion and thus completing the bridge to the carrier. A non-limiting example of a therapeutic agent is a peptide or protein.

Examples of active peptides/proteins include Insulin, growth factors, hormones, cytokines, growth hormone (GH, somatropin), nerve growth factor (NGF), brain-derived neurotrophic factor (BDNF), enzymes, endostatin, angiostatin, trombospondin, urokinase, interferon, blood clotting factors (VII, VIII), any molecule able to bind metal ions.

Sustained Release

If a subject biocompatible composition is formulated with an active agent, release of such an active agent for a sustained or extended period as compared to the release from an isotonic saline solution generally results. Such release profile may result in prolonged delivery (over, say 1 to about 4,000 hours, or alternatively about 4 to about 1500 hours) of effective amounts (e.g., about 0.00001 mg/kg/hour to about 10 mg/kg/hour) of the active agent or any other material associated with the biocompatible composition.

A variety of factors may affect the desired rate of dissociation of the active agent of the subject invention, the desired softness and flexibility of the biocompatible composition, rate and extent of active agent release. Some of such factors include: the selection of various coordinating groups on the metal ion, or, when the carrier is a polymer, the enantiomeric or diastereomeric purity of the monomeric subunits, homogeneity of subunits found in the polymer, and the length of the polymer. For instance, the present invention contemplates heteropolymers with varying linkages, and/or the inclusion of other monomeric elements in the polymer, in order to control, for example, the rate of active agent release of the subject compostion.

To illustrate further, a wide range of dissociation rates may be obtained by adjusting the hydrophobicities of the backbones or side chains of the polymers while still maintaining sufficient biodegradability for the use intended for any such polymer. Such a result may be achieved by varying the various functional groups of the polymer. For example, the combination of a hydrophobic backbone and a hydrophilic metal ion containing bridges between the carrier and active agent produces heterogeneous release because dissociation is encouraged whereas water penetration is resisted.

One protocol generally accepted in the field that may be used to determine the release rate of any active agent or other material attached to the carrier through a metal ion bridge of the present invention involves dissociation of any such active agent or other material in a 0.1 M PBS solution (pH 7.4) at 37° C., an assay known in the art. For purposes of the present invention, the term "PBS protocol" is used herein to refer to such protocol.

In certain instances, the release rates of different polymer systems of the present invention may be compared by subjecting them to such a protocol. In certain instances, it may be necessary to process polymeric systems in the same fashion to allow direct and relatively accurate comparisons of different systems to be made. Such comparisons may indicate that any one polymeric system releases the active agent at a rate from about 2 or less to about 1000 or more times faster than another polymeric system. Alternatively, a comparison may reveal a rate difference of about 3, 5, 7, 10, 25, 50, 100, 250, 500 or 750. Even higher rate differences are contemplated by the present invention and release rate protocols.

In certain embodiments, when formulated in a certain manner, the release rate for polymer systems of the present invention may present as mono- or bi-phasic. Release of any material incorporated into the polymer carrier, which may be provided as a microsphere, may be characterized in certain instances by an initial increased release rate, which may release from about 5 to about 50% or more of the active agent or alternatively about 10, 15, 20, 25, 30 or 40%, followed by a release rate of lesser magnitude.

The release rate of the active agent may also be characterized by the amount of such material released per day per mg of carrier. For example, in certain embodiments, when the carrier is a polymer, the release rate may vary from about 1 ng or less of active agent per day per mg of polymeric system to about 5000 or more ng/day/mg. Alternatively, the release rate may be about 10, 25, 50, 75, 100, 125, 150, 175, 200, 250, 300, 350, 400, 450, 500, 600, 700, 800 or 900 ng/day/mg. In still other embodiments, the release rate of the active agent may be 10,000 ng/day/mg or even higher. In certain instances, active agents characterized by such release rate protocols may include therapeutic agents, antigens, diagnostics, targeting moieties and other substances.

In another aspect, the rate of release of an active agent from any carrier of the present invention may be presented as the half-life of such material in the such matrix.

In addition to the embodiment involving protocols for in vitro determination of release rates, in vivo protocols, whereby in certain instances release rates of active agents from the carrier may be determined in vivo, are also contemplated by the present invention. Other assays useful for determining the release of active agents from the carriers of the present invention may be envisoned.

Dosages

The dosage of any compound of the present invention will vary depending on the symptoms, age and body weight of the patient, the nature and severity of the disorder to be treated or prevented, the route of administration, and the form of the supplement. Any of the subject formulations may be administered in a single dose or in divided doses. Dosages for the compounds of the present invention may be readily determined by techniques known to those of skill in the art or as taught herein. Also, the present invention contemplates mixtures of more than one subject compound, as well as other therapeutic agents.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular compound of the present invention. This may be accomplished by routine experiment as described herein, using one or more groups of animals (preferably at least 5 animals per group), or in human trials if appropriate. The effectiveness of any compound and method of treatment or prevention may be assessed by administering the supplement and assessing the effect of the administration by measuring one or more indices associated with the neoplasm of interest, and comparing the post-treatment values of these indices to the values of the same indices prior to treatment.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present invention, or alternatively other chemotherapeutic agents, may reduce the required dosage for any individual component because the onset and duration of effect of the different components may be complimentary. In such combined therapy, the different active agents may be delivered together or separately, and simultaneously or at different times within the day.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

Formulation

The compounds of the present invention may be administered by various means, depending on their intended use, as is well known in the art. For example, if compounds of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compounds of the present invention may be formulated as eyedrops or eye ointments. These formulations may be prepared by conventional means, and, if desired, the compounds may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compounds may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of agent that may be combined with a carrier material to produce a single dose vary depending upon the subject being treated, and the particular mode of administration.

Methods of preparing these formulations include the step of bringing into association agents of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound thereof as an active ingredient. Compounds of the present invention may also be administered as a bolus, electuary, or paste.

In solid dosage forms for oral administration (capsules, tablets, pills, dragees, powders, granules and the like), the coordination complex thereof is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the supplement or components thereof moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the compound, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a coordination complex of the present invention with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a supplement or component includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. For transdermal administration of transition metal complexes, the complexes may include lipophilic and hydrophilic groups to achieve the desired water solubility and transport properties.

The ointments, pastes, creams and gels may contain, in addition to a supplement or components thereof, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a supplement or components thereof, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compound.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise one or more components of a supplement in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Kits

This invention also provides kits for conveniently and effectively implementing the methods of this invention. Such kits comprise any of the compounds of the present invention or a combination thereof, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

EXEMPLIFICATION

The invention is further illustrated by the following Examples. The Examples are provided for illustrative purposes only, and are not to be construed as limiting the scope or content of the invention in any way.

Example 1

Synthesis of MPEG-PL

Poly-L-lysine, hydrobromide (Sigma, mol mass. 48000, d.p. 200), 1 g was dissolved in 175 ml of 0.1 M $Na_2CO_3$, pH 8.7. An aliquot of this solution was removed for $NH_2$-groups determination by TNBS titration (final concentration of $NH_2$-groups, 25 mM). Methoxy polyethylene glycol succinate (MPEGS 9.6 g, 1.9 mmol) was dissolved in 25 ml of water, degassed, and N-hydroxy(sulfo)succinimide (500 mg, 2.3 mmol) was added, followed by 1 g, 5 mmol of EDC in 2 ml of water. This solution was incubated for 10 min at room temperature and added drop-wise to the solution of poly-1-lysine, final pH 7.7. The mixture was incubated for six hours. The product was purified using ultrafiltration on a cartridge with a cut-off of 100 kD (UFP-100 A/G Technology) to remove unconjugated MPEGS and other reactants.

Example 2

Synthesis of MPEG-PL-NTA

The product obtained as described in Example 1 (MPEG-succinyl-poly-L-Lys (m.w. 340000) was succinylated using 10-fold molar excess of succinic anhydride over the concentration of TNBS-reactive free aminogroups in the co-polymer in 0.5 M sodium carbonate pH 8.0, 4 hours room temperature. Succinylated co-polymer (MPEGs-PL-Suc) was purified using dialysis against water.

100 mg Lyophilized MPEGs-PL-Suc was dissolved in 2 ml water at 28 µmol succinate/ml, treated with 30 mg ethyl-diaminopropyl carbodiimide (EDC) in the presence of 20 mg Sulfo-NHS for 10 min at room temperature. A solution of activated MPEGs-PL-Suc was added to a solution of N,N-Bis (carboxymethyl)-L-lysine Hydrate (BCMLys) in 1 ml sodium bicarbonate, pH 8.7. Final pH 7.6, incubated 24 hours at 4° C. The resultant product MPEGs-PL-Suc-NTA was purified using ultrafiltration on YM50 membrane (Amicon) by diluting to 100 ml and concentrating to 5 ml volume four times.

A solution of MPEGs-PL-Suc was used as a control in further experiments.

Example 3

Synthesis of MPEGs-PL-NiNTA

A solution of product MPEGs-PL-Suc-NTA was dialysed against 1 L of 10 mM Ni acetate/20 mM citric acid, pH 6 for 24 hours at 4° C. and purified by dialysing against 2 L water (2 changes). Binding of Ni was measured by spectrophotometry at 625 nm using Ni-citrate as a standard.

Example 4

Synthesis of MPEGs-PL-ZnNTA

A solution of MPEGs-PL-Suc-NTA was dialysed against 1 L of 10 mM Zn acetate/20 mM citric acid, pH 6 for 24 hours at 4° C. and purified by dialysing against 2 L water (2 changes). Binding of Zn was measured by using elemental analysis.

Example 5

Binding of rhGH to MPEGs-PL-Zn/NiNTA

500 µg rhGH were mixed with 40 µl radioactively labeled trace amounts of 125I-rhGH (concentration—5 mg/ml). Centricon YM100 was used to remove rhGH aggregates (flow-through collected). Final [rhGH]=3.22 mg/ml. Various amounts of MPEGs-PL-Zn/NiNTA were incubated with 20 µg rhGH in a volume of 100 µl. Unbound rhGH was removed on Centricon YM 100. Membrane-retained GH-MPEGs-PL-Ni/ZnNTA complex was washed with 100 µl PBS by centrifugation. Radioactivity in eluate and retentate were determined separately using a gamma counter (Table 1):

TABLE 1

Binding of labeled rhGH (20 µg) to various amounts of experimental and control copolymer complexes with Ni and Zn.

| Sample, chelate attached to MPEG-PL-Suc and carrier amount | The fraction of rGH retained on YM100 membrane | µg bound | µg bound minus background |
|---|---|---|---|
| Membrane control | 0.05 | 1.03 | control |
| sucNi, 1 mg | 0.05 | 1.04 | 0.01 |
| sucNi, 2 mg | 0.06 | 1.29 | 0.25 |
| ZnNTA, 1 mg | 0.11 | 2.26 | 1.22 |
| ZnNTA, 2 mg | 0.25 | 5.05 | 4.02 |
| NiNTA, 1 mg | 0.10 | 2.05 | 1.01 |
| NiNTA, 2 mg | 0.23 | 4.63 | 3.60 |

Non-specific binding to YM100 membrane surface and binding to succinylated control (compound I of Example 1) polymers were similar. Ni and Zn complexes of MPEGs-PL-NTA showed 12 to 20-fold higher binding (2 mg polymer in the incubation mixture):

Example 6

Size-exclusion Analysis of rhGH Complex with MPEGs-PL-ZnNTA

Figure 2:
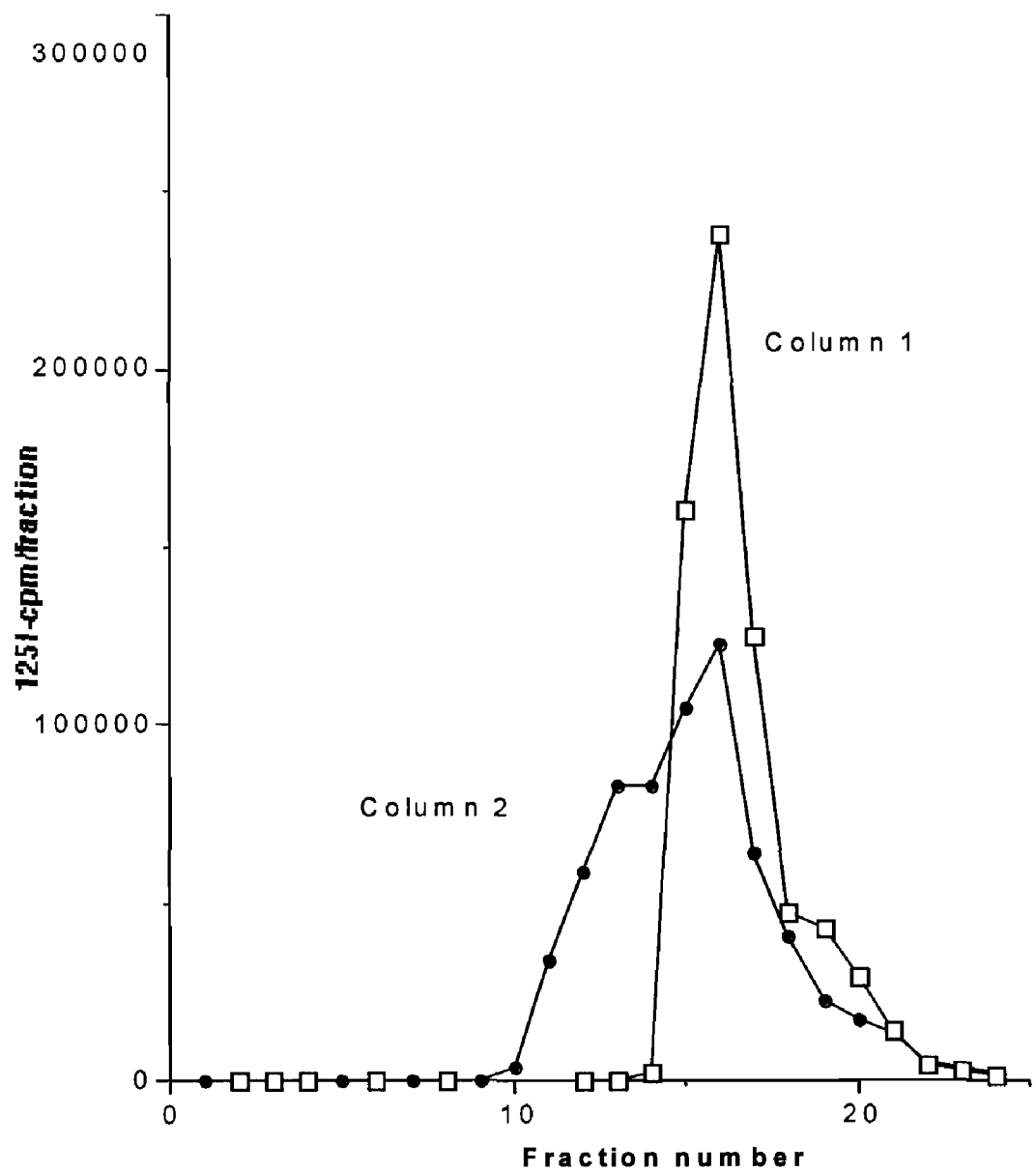
FIG. 2 depicts a chromatogram showing elution profiles of $^{125}$I-labled rhGH (squares) and rhGH complex with MPEGs-PL-ZnNTA (circles) on SEC-5 size-exclusion HPLC column. The profile of time-dependent elution shows that a fraction of the complex of labeled hormone with MPEGs-PL-ZnNTA elutes earlier than the free hormone suggesting a complex formation.

MPEGs-PL-Zn NTA complex (100 µl, 2 mg) was mixed with 100 µg rhGH and analyzed on size-exclusion HPLC column (SEC-5, Rainin). Fractions were collected and counted using a gamma-counter (FIG. 2). The formation of a complex between the co-polymer and rhGH is evident from a change in elution pattern (fractions 11-14 contain higher molecular weight complex).

Example 7

Construction of His-tagged Green Fluorescent Protein (GFP) Variant cDNA encoding for humanized GFP isoform was excised from BlueScriptGFP vector using compatible restriction sites. GFP fragment was then subcloned into SalI-KpnI-restricted pHAT10 vector (Clontech) to afford in-frame expression with His-tag (HAT™) from chicken lactate dehydrogenase (KNHLIHRVHKDDHAHAHRK) containing six histidines. Subcloning was performed by ligating the purified GFP fragment with linearized pHAT10 vector using T4 DNA ligase. Ligation reactions were used for *E. coli* transformation. Several colonies exhibiting bright green fluorescence under the UV light were selected. Bacterial colonies were transferred into LB broth and grown overnight in a volume of 5 ml. This starter culture was then used for infecting 1 l of LB medium grown to the density of 0.8 at 600 nm and bacterial culture was centrifuged at 6000 g to isolate bacterial mass. Bacteria were then lysed using B-PER buffer (Pierce) in the presence of 1× protease inhibitors (with no EDTA, Roche Biochemicals). Lysate was cleared by centrifugation at 16000×g (SS-34 Rotor, Sorvall) and the supernatant was combined with washed, pre-equilibrated TALON™ resin (Clontech). The mixture was agitated at 4 C overnight and washed several times with loading buffer (50 mM phosphate, 300 mM NaCl pH 7). Histidine tagged-GFP product was eluted using 100 mM imidazole in 45 mM Na-phosphate, 270 mM NaCl, pH 7). Fluorescent eluate was dialyzed against PBS, pH 7 and analyzed by electrophoresis.

Example 8

Binding of Histidine tagged-GFP to MPEG-PL-NTA and Control Polymers

Complex formation between NTA-conjugated MPEG-PL copolymer and histidine-tagged GFP was achieved by combining histidine tagged-GFP and $Ni^{2+}$ or $Zn^{2+}$ salts of MPEG-PL-NTA or MEPG-PL-succinate (control). After a 1 hour incubation the complexes were placed in YM-50 membrane. Various amounts of MPEGs-PLZn/NiNTA were incubated with 20 µg rhGH in a volume of 100 µl. Free non-bound histidine tagged-GFP was removed on Centricon YM100. Membrane-retained MPEGs-PL-Ni/ZnNTA complex was washed three times using 100 µl PBS aliquots by centrifugation. The fluorescence intensities in eluate and retentate were determined using a fluorometer (excitation 475, emission 510 nm). In some experiments, 100% mouse plasma was added to the incubation mixtures and samples were processed as described before.

TABLE 2

Binding of histidine tagged-GFP (20 µg) to 1 mg of MPEG-PL-NTA and a control polymer.

| Sample | % GFP bound |
| --- | --- |
| GFP control | 0.002 |
| MPEG-PL-succinate control | 0.003 |
| MPEG-PL-ZnNTA | 99.68 |
| MPEG-PL-NiNTA | 99.52 |

The obtained result shows that the binding of histidine tagged-GFP to metal chelates linked to MPEG-PL co-polymer was highly specific (Table 2) and that the association of HAT-GFP with similar co-polymer bearing no NTA residues was close to the background.

Figure 3:
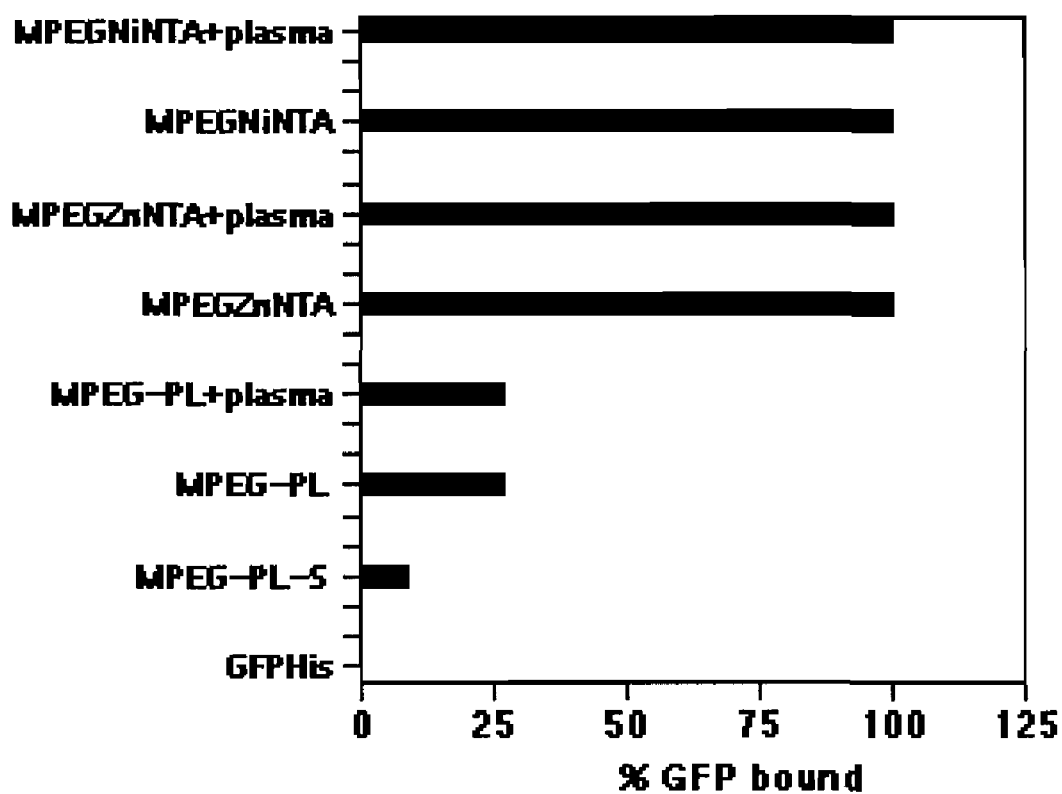
FIG. 3 depicts a bar-graph showing histidine tagged-GFP binding yields after separation of complexes with MPEGs-PL-NTA (Ni or Zn salts), MPEGs-PL or MPEGs-PL-succinate in the presence or absence of blood plasma. The graph shows that complex formation with metal salts of MPEGs-PL-NTA is equally possible in the presence or absence of bulk protein of plasma.
Figure 4:
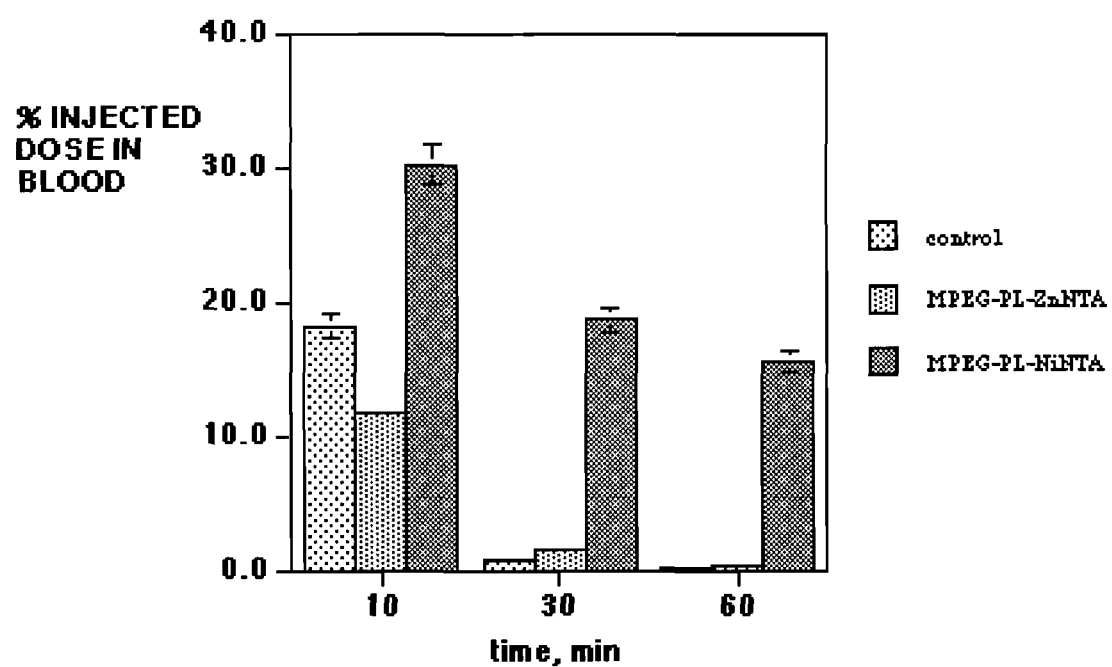
FIG. 4 depicts a bar graph showing the levels of GFP in plasma of animals injected with a histidine tagged-GFP (control); and complexes of histidine tagged-GFP with MPEGs-PL-ZnNTA and MPEGs-PL-NiNTA. The graph shows significantly higher in vivo levels of GFP in blood in the case of Ni-complex suggesting prolonged circulation of histidine tagged-GFP bound to MPEGs-PL-NiNTA carrier.

In the presence of plasma binding of histidine tagged-GFP was also highly specific. Binding to NTA-linked co-polymers in the presence of Ni and Zn cations was approximately the same in the presence or in the absence of the plasma. The only detectable non-specific binding levels were detectable in the case of polycationic MPEGs-PL co-polymer (FIG. 3) and this binding has not been inhibitable by plasma.

Example 9

Distribution of Histidine tagged-GFP and Histidine Tagged-GFP Complexes with MPEGs-PL-NTA in vivo After Intravenous Injection Pre-formed complexes of histidine tagged-GFP with MPEGs-PL-NiNTA and MPEGs-PL-ZnNTA as well as control histidine tagged-GFP were injected IV in the tail vein of anesthetized balb/c mice (20 µg histidine tagged-GFP mixed with 1 mg of co-polymer or 20 µg histidine tagged-GFP in a total volume of 0.1 ml, 2 per group) and blood samples were drawn through a catheter inserted in a contralateral tail vein. Blood samples (40 µl) were heparinized, centrifuged (3,000 g) and plasma samples were analyzed for histidine tagged-GFP using fluorometry (excitation-475/emission 508 nm). Observed fluorescence intensity values were normalized for injection dose using histidine tagged-GFP standard diluted in mouse plasma. The blood volume was calculated as 7% of animal weight and hematocrit—at 50%.

REFERENCES

Other than provisional application 60/360,350 identified in the first paragraph above, all publications and patents mentioned herein, including those items listed below, are hereby incorporated by reference in their entirety as if each individual publication or patent was specifically and individually incorporated by reference. In case of conflict, the present application, including any definitions herein, will control.

U.S. Pat. Nos. 6,395,299; 5,871,710; 5,763,585; 5,663,387; 5,605,672; 5,593,658; 5,593,658.

Equivalents

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A biocompatible composition comprising:
    a carrier with a first metal binding domain (MBD),
    a metal ion chelated to the first MBD,
    an active agent with a second MBD chelated to the metal ion, and
    one or more protective groups covalently bonded to the carrier
    wherein the first MBD, the metal ion, and the second MBD form a metal ion bridge and wherein after administration of the composition to a patient, the active agent is released from the composition.

2. The composition of claim 1, wherein the carrier is selected from a polymer, micelle, reverse micelle, liposome, emulsion, hydrogel, microparticle, nanoparticle, microsphere, or solid surface.

3. The composition of claim 1, wherein the carrier is a polymer.

4. The composition of claim 1, wherein the protective group is selected from poly(ethylene glycol), methoxy poly (ethylene glycol), dicarboxylic acid esterified poly (ethylene glycol) monoester, dicarboxylic acid esterified poly(propylene glycol) monoester, poly(ethylene glycol)-diacid, poly (propylene glycol)-diacid copolymer of poly(ethylene glycol), copolymer of poly (propylene glycol), poly(ethylene glycol) monoamine, poly(propylene glycol) monoamine, methoxy poly(ethylene glycol) monoamine, methoxy poly (propylene glycol) monoamine, methoxy poly(ethylene glycol) hydrazide, methoxy poly(propylene glycol) hydrazide, methoxy poly(ethylene glycol) imidazolide, methoxy poly (proylene glycol) imidazolide, blockcopolymer of poly (ethylene glycol), poly-lactideglycolide co-polymer, and polysaccharide.

5. The composition of claim 1, wherein the protective group comprises poly(ethylene glycol).

6. The composition of claim 1, wherein the protective group comprises alkoxy poly(ethyleneglycol).

7. The composition of claim 1, wherein the protective group comprises methoxy poly(ethyleneglycol) (MPEG).

8. The composition of claim 3, wherein the polymer is not a polyamino acid polymer.

9. The composition of claim 3, wherein the polymer has a molecular mass ranging from about 100 to about 1,000,000 daltons.

10. The composition of claim 3, wherein the polymer has a molecular mass ranging from about 10,000 to about 250,000 daltons.

11. The composition of claim 3, wherein the polymer is selected from galacturonic acid, glucuronic acid, mannuronic acid, hyaluronic acid, pectic acid, neuraminic acid, alginic acid, carrageenan, oxidized dextrans, linear or branched polysaccharides, linear or branched oligosaccharides, dextran, mannan, xylan, pullulan, cellulose,chytosan, agarose, fucoidan, galactan, arabinan, fructan, fucan, chitin, pustulan, levan, and pectin.

12. The composition of claim 11, wherein the polysaccharides or oligosaccharides are aminated, carboxylated, carboxymethylated, sulfated, or phosphorylated.

13. The composition of claim 3, wherein the first or second MBD comprises a nitrogen containing poly carboxylic acid.

14. The composition of claim 3, wherein the first or second MBD comprises one or more of the following:
N-(hydroxy-ethyl)ethylenediarninetriacetic acid; nitrilotriacetic acid (NTA);
ethylene-bis(oxyethylene-nitrilo)tetraacetic acid;
1,4,7,10-tetraazacyclodo-decane-N,N',N'',N'''tetraacetic acid;
1,4,7,10-tetraaza-cyclododecane-N,N',N''-triacetic acid;
1,4,7-tris(carboxymethyl)-10-(2'-hydroxypropy1)-1,4,7, 10-tetraazocyclodecane;
1,4,7-triazacyclonane-N,N',N''-triacetic acid;
1,4,8,11-tetraazacyclotetra-decane-N,N',N'',N'''-tetraacetic acid;
diethylenetriamine-pentaacetic acid (DTPA);
ethy lenedicysteine;
bis(aminoethanethiol)carboxy lie acid;
triethy lenetetraamine-hexaacetic acid;
ethylenediamine-tetraacetic acid (EDTA);
1,2-diaminocyclohexane-N,N',N',N'-tetraacetic acid; or polypeptide.

15. The composition of the claim 14, wherein the first or second MBD comprises a polypeptide of formula (AxHy)p, wherein A is any amino acid residue, H is histidine, x is an integer from 0-6, y is an integer from 1-6, and p is an integer from 1-6.

16. The composition of claim 3, wherein the metal ion is a transition metal ion.

17. The composition of claim 3, wherein the metal ion is one or more of the following: $Zn^{2+}$, $Ni^{2+}$, $Co^{2+}$, $Fe^{2+}$, $Mn^{2+}$, or $Cu^{2+}$.

18. The composition of claim 3, wherein the active agent is a diagnostic, targeting moiety, antigen or therapeutic agent.

19. The composition of claim 3, wherein more than one type of active agent is present.

20. The composition of claim 3, wherein the active agent comprises one or more of the following: a protein, peptide, peptidomimetic, antibody, chemotactic protein, or enzyme.

21. The composition of claim 3, wherein the active agent is selected from the group consisting of factor VII, factor VIII, insulin, growth factors, hormones, cytokines, growth hormones, nerve growth factor, brain-derived neurotrophic factor, endostatin, angiostatin, trombospondin, urokinase, colony stimulating factor and interferon.

22. A pharmaceutical composition comprising the composition of claim 3 and a pharmaceutically acceptable excipient or diluent.

23. The composition of claim 3, wherein the active agent is an imaging agent.

24. A kit comprising the composition of claim 3 and instructions for administering the composition to a patient.

* * * * *

UNITED STATES PATENT AND TRADEMARK OFFICE
CERTIFICATE OF CORRECTION

| | | |
|---|---|---|
| PATENT NO. | : 7,790,140 B2 | Page 1 of 1 |
| APPLICATION NO. | : 11/428803 | |
| DATED | : September 7, 2010 | |
| INVENTOR(S) | : Elijah M. Bolotin | |

It is certified that error appears in the above-identified patent and that said Letters Patent is hereby corrected as shown below:

In Column 45, Line 29, Claim 11; please replace "cellulose,chytosan" with --cellulose, chytosan--.

In Column 46, Lines 7-9, Claim 14; please replace "ethy lenedicysteine; bis(aminoethanethiol)carboxy lie acid; triethy lenetetraamine hexaacetic acid" with --ethylenedicysteine; bis(aminoethanethiol)carboxylic acid; triethylenetetraamine-hexaacetic acid--.

In Column 46, Line 13, Claim 15; after "composition of" please remove "the".

Signed and Sealed this
Twenty-sixth Day of June, 2012

David J. Kappos
*Director of the United States Patent and Trademark Office*